(12) United States Patent
Kang et al.

(10) Patent No.: US 9,408,873 B2
(45) Date of Patent: Aug. 9, 2016

(54) PHARMACEUTICAL COMPOSITION COMPRISING STEM CELLS TREATED WITH NOD2 AGONIST OR CULTURE THEREOF FOR PREVENTION AND TREATMENT OF IMMUNE DISORDERS AND INFLAMMATORY DISEASES

(75) Inventors: Kyung Sun Kang, Seoul (KR); Hyung Sik Kim, Seoul (KR)

(73) Assignee: KANG STEM BIOTECH CO., LTD., Seoul (KR)

( * ) Notice: Subject to any disclaimer, the term of this patent is extended or adjusted under 35 U.S.C. 154(b) by 0 days.

(21) Appl. No.: 13/818,234

(22) PCT Filed: Aug. 19, 2011

(86) PCT No.: PCT/KR2011/006109

§ 371 (c)(1),
(2), (4) Date: Apr. 9, 2013

(87) PCT Pub. No.: WO2012/026712

PCT Pub. Date: Mar. 1, 2012

(65) Prior Publication Data

US 2013/0209422 A1 Aug. 15, 2013

(30) Foreign Application Priority Data

Aug. 23, 2010 (KR) .................. 10-2010-0081640

(51) Int. Cl.
*A61K 35/28* (2015.01)
*A61K 35/545* (2015.01)
(Continued)

(52) U.S. Cl.
CPC ............... *A61K 35/28* (2013.01); *A61K 35/545* (2013.01); *A61K 38/05* (2013.01); *C12N 5/0665* (2013.01);
(Continued)

(58) Field of Classification Search
None
See application file for complete search history.

(56) References Cited

U.S. PATENT DOCUMENTS 5,753,234 A 5/1998 Lee et al.
2007/0041997 A1 2/2007 Finlay et al.
(Continued)

FOREIGN PATENT DOCUMENTS

JP H11503426 A 3/1999
WO WO 2006109300 A1 * 10/2006
(Continued)

OTHER PUBLICATIONS

Hyung-Sik Kim, Tae-Hoon Shin, Se-Ran Yang, Min-Soo Seo, Dong-Jae Kim, Soo-Kyung Kang, Jong-Hwan Park, Kyung-Sun Kang, Implication of NOD1 and NOD2 for the Differentiation of Multipotent Mesenchymal Stem Cells Derived from Human Umbilical Cord Blood, 2010, PLoS One, Oct. 2010, vol. 5, Issue 10, e15369, pp. 1-7.*

(Continued)

*Primary Examiner* — Ralph Gitomer
*Assistant Examiner* — Trent Clarke
(74) *Attorney, Agent, or Firm* — Edwin S. Flores; Chainey P Singleton; Chalker Flores, LLP

(57) ABSTRACT

The present invention relates to a pharmaceutical composition for the prevention or treatment of immune disorders and inflammatory diseases, comprising stem cells that are generated by culturing stem cells expression Nucleotide-binding Oligomerization Domain protein 2 (NOD2) with a NOD2 agonist or a culture thereof. More particularly, the present invention relates to a method for suppressing immune responses or inflammatory responses of a subject, comprising the step of administering the pharmaceutical composition, the stem cells or culture thereof to the subject, a method for preparing an immunosuppressive drug or an anti-inflammatory drug using the stem cells or culture thereof, a method for preparing $PGE_2$ or TGF-β1 comprising the step of culturing NOD2-expressing stem cells in culture medium with a NOD2 agonist, a graft comprising stem cells expressing NOD2 and the NOD2 agonist, a method for preparing the graft, a composite comprising stem cells expressing NOD2 and the NOD2 agonist, and a culture generated by culturing the NOD2-expressing stem cells with a NOD2 agonist.

7 Claims, 30 Drawing Sheets

(51) Int. Cl.
*A61K 38/05* (2006.01)
*C12N 5/0775* (2010.01)

(52) U.S. Cl.
CPC ......... *C12N 2501/02* (2013.01); *C12N 2501/05* (2013.01); *C12N 2501/052* (2013.01); *C12N 2501/054* (2013.01)

(56) References Cited

U.S. PATENT DOCUMENTS

| | | | |
|---|---|---|---|
| 2009/0169522 | A1 | 7/2009 | Danilkovitch et al. |
| 2009/0202479 | A1 | 8/2009 | Shi et al. |
| 2011/0182974 | A1 | 7/2011 | Ben-Yedidia et al. |

FOREIGN PATENT DOCUMENTS

| | | |
|---|---|---|
| WO | 2008070564 A1 | 6/2008 |
| WO | 2009/007979 A2 | 1/2009 |
| WO | 2009114860 A2 | 9/2009 |
| WO | 2009129616 A1 | 10/2009 |

OTHER PUBLICATIONS

Mouldy Sioud and Yngvar Fløisand, NOD2/CARD15 on bone marrow CD34 hematopoietic cells mediates induction of cytokines and cell differentiation, 2009, Journal of Leukocyte Biology, vol. 85, pp. 939-946.*

Wagner et al, Comparative characteristics of mesenchymal stem cells from human bone marrow, adipose tissue, and umbilical cord blood, 2005, Experimental Hematology, vol. 33, pp. 1402-1416.*

Borzutzky, A., et al., "NOD2-associated diseases: Bridging innate immunity and autoinflammation," Clinical Immunology (2010) 134:251-261.

Girardin, S., et al., "Nod2 is a General Sensor of Peptidoglycan through Muramyl Dipeptide (MDP) Detection", The Journal of Biological Chemistry (2003) 278:11 8869-8872.

Glennie, S., et al., "Bone marrow mesenchymal stem cells induce division arrest anergy of activated T cells," Blood (2005) 105:2821-2827.

Goodwin, J.S., et al., "Regulation of the Immune Response by Prostaglandins," Journal of Clinical Immunology (1983) 3:4, 295.

Harris, S., et al. "Prostaglandins as modulators of immunity," TRENDS in Immunology (2002) 23:3 144-150.

Hisamatsu, T., et al., "Interferon-y Arguments CARD4/NOD1 Gene and Protein Expression through Interferon Regulatory Factor-1 in Intestinal Epithelial Cells," The Journal of Biological Chemistry (2003) 278:35 32962-32968.

Ikehara, Susumu, "A novel strategy for allogeneic stem cell transplantation: perfusion method plus intra-bone marrow injection of stem cells," Experimental Hematology (2003) 1142-1146.

Ushikubi, F., et al., "Roles of Prostanoids Revealed From Studies Using Mice Lacking Specific Prostanoid Receptors," Jpn. J. Pharmacol. (2000) 83:279-285.

Najar, Mehdi, et al., "Mesenchymal stromal cells use PGE2 to modulate activation and proliferatoion of lymphocyte subsets: Combined comparison of adipose tissue, Wharton's Jelly and bone marrow sources," Cellular Immunology. vol. 264, pp. 171-179(Jun. 18, 2010).

Keith D., et al., "Mesenchymal stem cells produce Wnt isoforms and TGF-B1 that mediate proliferation and procollagen expression by ling fibroblasts," American Journal of Physiology—Lung Cellular and Molecular Physiology. vol. 297, pp. L1 002-L1 01 1(2009) Salazar et al.

Koreth, John, et al., ":Current and future approaches for control of graft-versus-host disease," Expert Review of Hematology. vol. 1, pp. 111-128(2008).

Office Action from Korean Patent Office dated Apr. 18, 2013 for Korean Application No. 10-2011-0082687and English Translation of same.

Sioud, Mouldy et al., "NOD2/CARD15 on bone marrow CD34+ hematopietic cells mediates induction of cytokines and cell differentiation," Journal of Leukocyte Biology (Jun. 2009) vol. 85, pp. 939-946.

Ryan, J.M. et al., "Interferon-y does not break, but promotes the immunosuppressive capacity of adult human mesenchymal stem cells," Clinical and Experimental Immunology (2007) vol. 149, pp. 353-363.

\* cited by examiner

*, significantly different from Df group (p<0.05).

*, significantly different from Df group (p<0.05).

*, significantly different from Df group (p<0.05).

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: TLR2 Forward primer

<400> SEQUENCE: 1
gatgcctact gggtggagaa                                              20

<210> SEQ ID NO 2
```

```
<211> LENGTH: 20
<212> TYPE: DNA
<213> ORGANISM: Artificial Sequence
<220> FEATURE:
<223> OTHER INFORMATION: TLR2 Reverse primer

<400> SEQUENCE: 2
cgcagctctc agatttaccc                                               20

<210> SEQ ID NO 3
<211> LENGTH: 19
<212> TYPE: DNA
<213> ORGANISM: Artificial Sequence
<220> FEATURE:
<223> OTHER INFORMATION: TLR4 Forward primer

<400> SEQUENCE: 3
acagaagctg gtggctgtg                                                19

<210> SEQ ID NO 4
<211> LENGTH: 21
<212> TYPE: DNA
<213> ORGANISM: Artificial Sequence
<220> FEATURE:
<223> OTHER INFORMATION: TLR4 Reverse primer

<400> SEQUENCE: 4
tctttaaatg cacctggttg g                                             21

<210> SEQ ID NO 5
<211> LENGTH: 20
<212> TYPE: DNA
<213> ORGANISM: Artificial Sequence
<220> FEATURE:
<223> OTHER INFORMATION: NOD1 Forward primer

<400> SEQUENCE: 5
ccacttcaca gctggagaca                                               20

<210> SEQ ID NO 6
<211> LENGTH: 20
<212> TYPE: DNA
<213> ORGANISM: Artificial Sequence
<220> FEATURE:
<223> OTHER INFORMATION: NOD1 Reverse primer

<400> SEQUENCE: 6
tgagtggaag cagcattttg                                               20

<210> SEQ ID NO 7
<211> LENGTH: 20
<212> TYPE: DNA
<213> ORGANISM: Artificial Sequence
<220> FEATURE:
<223> OTHER INFORMATION: NOD2 Forward primer

<400> SEQUENCE: 7
gaatgttggg cacctcaagt                                               20

<210> SEQ ID NO 8
<211> LENGTH: 20
<212> TYPE: DNA
<213> ORGANISM: Artificial Sequence
<220> FEATURE:
<223> OTHER INFORMATION: NOD2 Reverse primer

<400> SEQUENCE: 8
```

```
caaggagctt agccatggag                                              20

<210> SEQ ID NO 9
<211> LENGTH: 20
<212> TYPE: DNA
<213> ORGANISM: Artificial Sequence
<220> FEATURE:
<223> OTHER INFORMATION: Rip2 Forward primer

<400> SEQUENCE: 9
ccattgagat ttcgcatcct                                              20

<210> SEQ ID NO 10
<211> LENGTH: 20
<212> TYPE: DNA
<213> ORGANISM: Artificial Sequence
<220> FEATURE:
<223> OTHER INFORMATION: Rip2 Reverse primer

<400> SEQUENCE: 10
atgcgccact ttgataaacc                                              20

<210> SEQ ID NO 11
<211> LENGTH: 20
<212> TYPE: DNA
<213> ORGANISM: Artificial Sequence
<220> FEATURE:
<223> OTHER INFORMATION: RPL13A Forward primer

<400> SEQUENCE: 11
catcgtggct aaacaggtac                                              20

<210> SEQ ID NO 12
<211> LENGTH: 20
<212> TYPE: DNA
<213> ORGANISM: Artificial Sequence
<220> FEATURE:
<223> OTHER INFORMATION: RPL13A Reverse primer

<400> SEQUENCE: 12
gcacgacctt gagggcagcc                                              20
```

PHARMACEUTICAL COMPOSITION COMPRISING STEM CELLS TREATED WITH NOD2 AGONIST OR CULTURE THEREOF FOR PREVENTION AND TREATMENT OF IMMUNE DISORDERS AND INFLAMMATORY DISEASES

BACKGROUND OF THE INVENTION

1. Field of the Invention

The present invention relates to a pharmaceutical composition for the prevention or treatment of immune disorders and inflammatory diseases, comprising stem cells that are generated by culturing stem cells expressing Nucleotide-binding Oligomerization Domain protein 2 (NOD2) with a NOD2 agonist or a culture thereof. More particularly, the present invention relates to a method for suppressing immune responses or inflammatory responses of a subject, comprising the step of administering the pharmaceutical composition, the stem cells or culture thereof to the subject, a method for preparing an immunosuppressive drug or an anti-inflammatory drug using the stem cells or culture thereof, a method far preparing $PGE_2$ or TGF-β1 comprising the step of culturing NOD2-expressing stem cells in culture medium with a NOD2 agonist, a graft comprising stem cells expressing NOD2 and the NOD2 agonist, a method for preparing the graft, a composite comprising stem cells expressing NOD2 and the NOD2 agonist, and a culture generated by culturing the NOD2-expressing stem cells with a NOD2 agonist.

2. Description of the Related Art

Proteins that belong to a Nucleotide-binding Oligomerization Domain (NOD) protein family are composed of three main domains: a caspase-recruitment domain (CARD) or pyrin domain at N-terminal which is involved in a protein-protein interaction, a central NOD domain, and a LPR domain at C-terminal. Types of NOD proteins can be divided into a NOD1 group which has one CARD domain at N-terminal and a NOD2 group which has two CARD domains at N-terminal. These two groups are are together called NOD-like receptor (NLR), and they contribute significantly to the development of immune response in vivo, along with a Toll-like receptor (TLR). NOD is known to play a vital role in an innate immune response by recognizing PGN moiety from the cell walls of most bacteria. NOD1 is expressed in epithelia cells of stomach and colon and in macrophages and dendritic cells of pancreas, lungs, kidney, and spleen. NOD1 is known to recognize a diaminopimelic acid (DAP)-type PGN stem peptide, dipeptide or tripeptide, which is present in dram-negative bacteria and a few gram positive bacteria, but absent in eukaryotes (Hisamatsu T et al. J. Biol. Chem., 278:32962, 2003).

NOD2 is expressed predominantly in myeloid cells, particularly macrophages, neutrophils, and dendritic cells, as well as in Paneth cells in the small intestine, and its distribution is more restricted than NOD1. Furthermore, the expression of NOD2 is induced by the inflammatory cytokines, i.e., TNF-alpha and IFN-gamma. As a result, NOD2 is barely expressed in the normal enterocytes, but is expressed only when the enterocytes are infected. The most widely known agonist (ligand) among the ones that are recognized by NOD2 is a muramyl dipeptide (MDP), which is the peptidoglycan (PGN) motif common to both of gram-negative and gram-positive bacteria (Girardin S E, et al., J. Biol. Chem., 278: 8369, 2003).

In 2003, Girardin, S. E. et al. reported that NOD2-knockout mice can grow normally, but became highly sensitive to an infection by oral, but not intravenous, administration of *Listeria monocytogenes*. This result suggests that NOD2 is not involved in a growth mechanism but instead serves as a pattern recognition protein sensing the presence of MDP. However, in the presence of *Listeria* strain in intestine, NOD2 induces an innate, immune response of antibacterial activity acting as a defense protein in the body (Girardin S E, et al., J. Biol. Chem., 278:8869, 2003). MDP has been used as an adjuvant for stimulating immune responses, i.e. antigenic adjuvant, and as an adjuvant capable of assisting an immunogen (Korean Patent Application Publication Nos. 1019960033469, 1020070031848, and 1020100045473).

Meanwhile, prostaglandin $E_2$ (hereinafter, referred to as $PGE_2$) is a compound represented by prostaglandin $E_2$: (5Z, 11(alpha),13E,15S)-11,15-dihydroxy-9-oxo-prosta-5,13-dien-1-oic acid, and is the most widely produced prostaglandin in physiological and pathological conditions (Ushikubi F et al., J. Pharmacol. Sci. 33:279, 2000).

$PGE_2$ was traditionally used to prepare the cervix for labor and has been actually used in pharmaceutical composition for stimulating childbirth. It is manufactured in a form of vaginal suppository with the following brand names: Cervidil (by Forest Laboratories, Inc.), Prostin E2 (by Pfizer Inc.), Propess (by Herring Pharmaceuticals) and Glandin (by Nabiqasim Pharmaceuticals Pakistan). Recently, $PGE_2$ has been suggested as a strong candidate for new immunosuppressive modulator, as it functions to suppress release of cytokines such as interleukin-1 beta and TNF alpha which are produced by macrophage and also to suppress helper T1 cell differentiation (Harris S G et al., Trends Immunol., 23:144, 2002). Furthermore, Furthermore, in vitro study has reported that $PGE_2$ inhibits production of cytokines such as interleukin-2 and IFN-gamma so as suppress human and marine differentiation (Goodwin J S et al., J. clin. Immunol., 3295, 1983). These studies suggest $PGE_2$ as a promising immunomodulatory drug, and as a result there has been a high need for development of a cost-effective and simple production method thereof.

Likewise, transforming growth factor beta 1 (TGF-β1) is known as an immunosuppressive and anti-inflammatory drug. TGF-β1, like $PGE_2$, has been suggested as a promising immunomodulatory drug, and as a result there has been a high need for development of a cost-effective and simple production method thereof.

Meanwhile, the types of immunosuppressive drugs can be divided into specific and non-specific immunosuppressants. Theoretically, specific immunosuppressants are superior, but non-specific immunosuppressants are mainly used. Cyclosporine (Neoral, Cipol A), Azathioprine (imuran), and Prednisolone (a steroid) are the most frequently used immunosuppressive drugs in clinical practice. It was found that a combination of these these three drugs showed fewer side effects and higher immunosuppressive effects than use of individual drug. Recently, many immunosuppressive drugs such as FK 506, RATG, OKT3, Cellcept, etc. have been developed and used in clinical practice.

In the process from antigenic stimulation to antibody production, these immunosuppressive drugs cause immunosuppression by hindering phagocytic processing of antigens by macrophages, antigen recognition by lymphocytes, cell division, division of T and B cells, or antibody production. Most of the drugs have an antitumor activity, as they hinder cell division by inducing DNA injury, inhibition of DNA synthesis and the like.

However, the representative side effects of the drugs are hypertension and nephrotoxicity (reduction in renal function). Due to high occurrence of these side effects, the conditions at the patients had to be monitored adequately to detect the occurrence, of the side effects. Side effects such as tremor, convulsion, hepatitis, cholestasis, hyperuricemia, muscle weakness, hypertrichosis, and gingival hypertrophy arise rarely. One of the frequently used suppressants called azathioprine suppresses bone marrow function incurring low leukocyte count, anemia, and low platelet, count. In addition, azathioprine may cause complications such as pancreatitis, hepatitis, and cholestasis, as well as hair loss and fever occasionally. A steroid drug called prednisolone is the first immunosuppressant used in the market and has a variety of suppressive activity. For instance, it can increase one's appetite, the amount of muscle around the shoulder and the back, and can cause temporary euphoria. However, this steroid drug should be carefully used, since it promotes the progression of atherosclerosis, and causes hypertension, gastric ulcer, diabetes, growth retardation, osteoporosis, cataract, or glaucoma.

Allogeneic transplantation such as organ transplantation and hematopoietic stem cell transplantation is a remarkable medical achievement in the 21st century, and has been applied for radical treatment of terminal diseases such as heart failure, including dilated cardiomyopathy, chronic renal failure, and intractable hematological disorders. However, there is still, a limitation to overcome lethal complications arising after allogeneic transplantation, such as engraftment failure or graft-versus-host-disease (GVHD), in an effort to minimize these immune responses, a therapy for controlling T cell immune responses has been used which are caused by cellular immunity by T cells recognizing allogenic antigens after transplantation (Ikehara S, Exp. Hematol., 31:1142, 2003; First M R, Transplantation, 77:88, 2004), that is, a therapy of controlling immune responses by suppressing interleukin (IL)-2 production of T cell using an immunosuppressive drug, Cyclosporine or FK506. However, there is still a high demand for the development of inexpensive immunosuppressive drugs with no side effects.

Meanwhile, the immune regulation mechanisms of mesenchymal stem cells have not been fully identified yet, while only a few studies have been reported regarding mesenchymal stem cells. The first finding was that mesenchymal mesenchymal stem cells appear to suppress antigen presenting cell (APC). Changes in immune responses are proportional to the number of monocytes added during the culturing process under certain conditions, suggesting that monocytes are involved in immune suppression. The second finding was that mesenchymal stem cells appear to induce immunosuppressive properties by regulating T cell proliferation. Co-culturing of of T cells with mesenchymal stem cells down-regulates the expression of cyclin D2 and subsequently arrests T cells in the G0/G1 phase of the cell cycle to prevent their proliferation. It was also reported that the proliferating ability is continuously reduced, even after mesenchymal stem cells are removed (Glennie S et al., Blood, 105:2821, 2005).

In an effort to develop more effective way of regulating immune or inflammatory responses using stem cells, the present inventors first found that NOD2 receptor is expressed in stem cells, and the stem cells regulate, immune responses is NOD2 receptor. Then they discovered that when the stem cells are treated with a NOD2 agonist i.e. MDP, $PGE_2$ and TGF-β1 are excessively expressed, leading to more effective suppression of the immune response, thereby demonstrating its therapeutic effects on colitis and atopic dermatitis models completed the present invention.

SUMMARY OF THE INVENTION

An object of the present invention is to provide a pharmaceutical composition for the prevention or treatment of immune disorders or inflammatory diseases, comprising stem cells that are generated by culturing stem cells expressing NOD2 with an NOD2 agonist or a culture thereof, which is inexpensive and has no side effect as an alternative to the conventional immunosuppressive drugs and anti-inflammatory drugs.

Another object of the present invention is to provide a method for treating immune disorders or inflammatory disease, comprising the step of administering the composition to a subject with immune disorders or inflammatory disease.

Still another object of the present invention is to provide a method for suppressing immune responses or inflammatory responses of a subject, comprising the step of administering the stem cells or the culture thereof to the subject.

Still another object of the present invention is to provide a method for preparing an immunosuppressive drug or anti-inflammatory drug.

Still another object of the present invention is to provide a method for preparing prostaglandin $E_2$ and TGF-β1 which are used in various applications.

Still another object of the present invention is to provide a graft comprising the stem cells expressing NOD2 and the NOD2 agonist, or a graft prepared by removing the stem cells from the graft, and a preparation method of the grafts.

Still another object of the present invention is to provide a composite comprising the stem cells expressing NOD2 and the NOD2 agonist.

Still another object of the present invention is to provide a culture that is generated by adding the NOD2 agonist to stem cells expressing NOD2.

DETAILED DESCRIPTION OF THE PREFERRED EMBODIMENTS

Figure 1A:
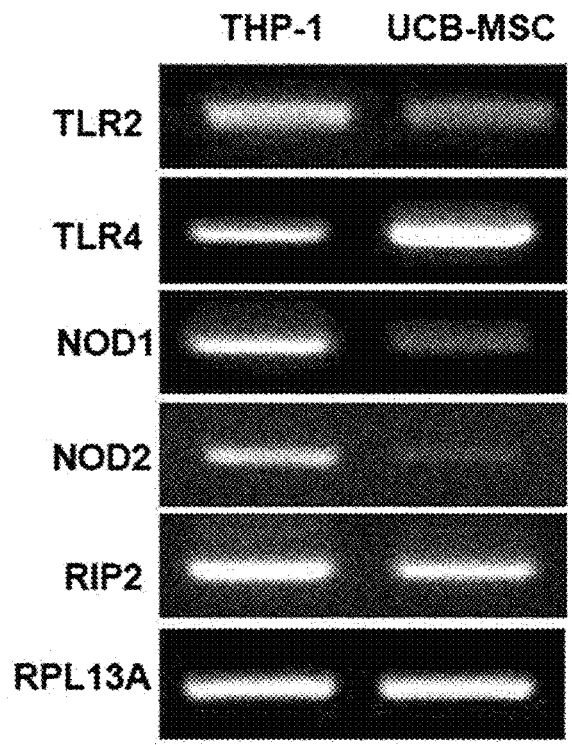
FIG. 1a shows the mRNA RT-PCP result demonstrating TLR and NLR expression in hUCB-MSC.

In one aspect to achieve the above objects, the present invention provides a pharmaceutical composition for the prevention or treatment of immune disorders or inflammatory diseases, comprising stem cells that are generated by culturing stem cells expressing Nucleotide-binding Oligomerization Domain protein 2 (NOD2) with a NOD2 agonist or a culture, thereof.

In the present invention, it was found that the treatment of stem cells with Nucleotide-binding Oligomerization Domain protein 2 (NOD2) agonist promotes the secretion of PGE$_2$ and TGF-β1 in the mesenchymal stem cells, which in turn regulates immune and inflammatory responses. In other words, the present present invention confirmed that immune and inflammation regulatory activity of stem cells are correlated with the function of NOD2, and immunosuppressive and anti-inflammatory effects are enhanced when treated with NOD2 agonist, and thus the NOD2 agonist-treated stem cells and a culture thereof can be used as a cellular therapeutic agent for immune and inflammation regulation. Therefore, the present invention provides a pharmaceutical composition for the prevention or treatment of immune disorders or inflammatory diseases, comprising stem cells that are generated by culturing stem cells expressing Nucleotide-binding Oligomerization Domain protein 2 (NOD2) with a NOD2 agonist or a culture thereof. As used herein, the terms 'NOD2' and 'NOD2 receptor' can be used interchangeably.

As used herein, the term 'agonist' generally refers to a chemical that functions to stimulate a receptor positively, and is also called an effector. In other words, an agonist has a positive function, while antagonist functions to hinder a ligand or has a negative function. In the present invention, the agonist can be used interchangeably with 'ligand' which refers to a chemical that binds to a receptor in general. With respect to the objects of the present invention, the agonist may be a NOD2 agonist.

As used herein, the term 'NOD2 agonist' refers to a substance that binds to a NOD2 receptor to activate NOD2, and one of the examples of NOD2 agonist is Muramyl Dipeptide (MDP) but is not limited thereto.

As used herein, the term 'MDP' is muramyl dipeptide, and in the present invention at can be used as an agonist that activates NOD2 pathway to promote secretion of PGE$_2$ in the mesenchymal stem cells.

As used herein, the phrases 'cultured with addition' or 'generated with addition' of agonist may refer to culturing of mesenchymal stem cells in a culture medium added with an agonist as an example. Preferably, the above culturing may refer to culturing with addition of the agonist at a concentration of 1 to 100 μg/ml for 0.1 to 200 hours, and more preferably for 1 to 72 hours. In addition, it may refer to culturing of the cells in the medium added with the agonist, and further culturing in the replaced medium.

As used herein, the term 'stem cells' refers to cells that have the capability to differentiate into various tissues, i.e., 'undifferentiated cells'. The term 'mesenchymal stem cells' refers to pluripotent stem cells derived from various adult cells such as bone marrow, umbilical cord blood, placenta (or placental tissue) and fat (adipose tissue). For example, mesenchymal stem cells derived from bone marrow possess a pluripotency to differentiate into adipose tissue, bone/cartilage tissue, and muscle tissue and thus many studies have focused on investigating mesenchymal stem cells for the development of cell therapy.

In the present invention, the stem cells may be human adult stem cells, human pluripotent stem cells, induced pluripotent stem cells, animal embryonic stem cells or animal adult stem cells. Meanwhile, the adult stem cells may be mesenchymal stem cells, human tissue-derived mesenchymal stromal cell, human tissue-derived mesenchymal stem cells, pluripotent stem cells or amniotic epithelial cells, and the mesenchymal stem cells may be mesenchymal stem cells derived from a source selected from the group consisting of umbilical cord, umbilical cord blood, bone marrow, fat, muscle, nerve, skin, amnion and placenta, and preferably those derived from human, and most preferably mesenchymal stem cells (hUCB-MSCs) derived from human umbilical cord blood. Obtaining stem cells from each source may be performed following the method known in the art, and is not limited to the method described, in Examples of the present invention.

Preferably, mesenchymal stem cells prepared by treatment of human-derived mesenchymal stem cells with MDP at a concentration of 1 to 100 µg/ml for 0.1-200 hours are used. If the cells are cultured with MDP for 0.1 hour or shorter, NOD2 pathway cannot be sufficiently activated. If the cells are cultured with MDP for 200 hours or longer, there are no financial benefits. Thus, mesenchymal stem cells are treated with MDP more preferably for 0.1~200 hours, much more preferably for 1~72 hours, and most preferably for 24 hours.

For culturing the mesenchymal stem cells, any conventional medium known in the art can be used that are known to be suitable for stem cell culturing. For example, Dulbecco's modified Eagle medium (DMEM) or Keratinocyte serum-free medium (Keratinocyte-SFM) may be used. Most preferably, D-media (Gibco) may be used.

The medium for culturing mesenchymal stem cells may be supplemented with additives. Generally, the medium may contain a neutral, buffer (e.g., phosphate and/or high concentration bicarbonate) in isotonic solution and a protein nutrient (e.g., serum such as FPS, serum replacement, albumin, or essential and non-essential amino acids such as glutamine). Furthermore, it may contain lipids (fatty acids, cholesterol, an HDL or LDL extract of serum) and other ingredients found in most stock media of this kind (e.g., insulin or transferrin, nucleosides or nucleotides, pyruvate, a sugar source such as glucose, selenium in any ionized form or salt, a glucocorticoid such as hydrocortisone and/or a reducing agent such as β-mercaptoethanol).

Also, with a view to protecting cells from adhering to each other or to a vessel wall, or from forming large clusters, it may be beneficial to include, an anti-clumping agent in the medium, for example, those sold by Invitrogen (Cat #0010057AE).

In one embodiment of the present invention, it was found that the culture of stem cells which were cultured with addition of one of NOD2 agonists, Muramyl Dipeptide (MDP) inhibits proliferation of mononuclear cells (MNC).

Mononuclear cells circulating in bloodstream migrate to tissues where they mature into macrophages. Mononuclear cells, macrophages, and dendritic cells are the most important ones in the body defense system, and have a central role in the initiation of adaptive immune responses having the ability to present antigen and regulate the function of T-lymphocyte. On the other hand, mononuclear cells and macrophage act as the primary defense barriers in immune system. Also, mononuclear cells function as accessory cells in the recognition and activation steps of adaptive immune responses. They function as antigen presenting cells (APCs) for antigen recognition by T-lymphocytes, and produce membrane proteins and secretory proteins that function as secondary sinners for T cell activation. Some of mononuclear phagocytes can differentiate into dendritic cells, which play an important role in stimulation, of T lymphocyte responses against protein antigens. When cell and organ transplant rejection occurs, the cell/organ transplanted in the body is recognized as a foreign object, and therefore, the number of mononuclear cells, macrophages, and dendritic cells all increase. Thus, it is apparent to those skilled in the art that suppression of the mononuclear cell proliferation by using the culture of stem cells generated with addition of Muramyl Dipeptide (MDP) leads to suppressor of immune responses in the body.

As used herein, the term 'mononuclear cell' refers to a mononuclear phagocytic leukocyte derived from the bone marrow and peripheral blood cells.

Furthermore, in another embodiment of the present invention, it was found that stem cells cultured with addition of Muramyl Dipeptide (MDP) promotes secretion of $PGE_2$ and TGF-β1, leading to MNC suppression that is induced by $PGE_2$ and TGF-β1. It has been reported that $PGE_2$ functions to inhibit the secretion of inflammatory cytokines such as interleukin-1 beta and cytokines TNF alpha, TGF-β1 is considered as an anti-inflammatory cytokine.

In still another embodiment of the present invention, it was suggested that MDP-treated stem cells produce an anti-inflammatory cytokine IL-10 at high yield, and furthermore, forms a regulatory T cell population.

Therefore, the stem cells of the present invention and the culture thereof are useful for the prevention or treatment of immune, disorders and inflammatory diseases. In this regard, the immune disorders or inflammatory diseases may be autoimmune diseases, transplant rejection, graft-versus-host-disease, arthritis, bacterial infection, sepsis, inflammation or the like. The autoimmune diseases may be Crohn's disease, erythema, atopic dermatitis, rheumatoid arthritis, Hashimoto's thyroiditis, pernicious anemia, Addison's disease, type 1 diabetes, lupus, chronic fatigue syndrome, fibromyalgia, hypothyroidism and hyperthyroidism, scleroderma, Behcet's disease, inflammatory bowel disease, multiple sclerosis, myasthenia gravis, Meniere's syndrome, Guillain-Barre syndrome, Sjogren's syndrome, vitiligo, endometriosis, psoriasis, vitiligo, systemic scleroderma, asthma, ulcerative colitis or the like.

As used herein, the term 'inflammatory diseases' collectively mean lesions caused by inflammation, and may be, but not limited to, preferably edema, dermatitis, allergy, atopic dermatitis, asthma, conjunctivitis, periodontitis, rhinitis, tympanitis, pharyngolarygitis, amygdalitis, pneumonia, gastric ulcer, gastritis, Crohn's disease, colitis, haemorrhoids, gout, ankylosing spondylitis, rheumatic fever, lupus, fibromyalgia, psoriatic arthritis, osteoarthritis, rheumatoid arthritis, Periarthritis of shoulder, tendonitis, tenosynovitis, myositis, hepatitis, cystitis, nephritis, sjogren's syndrome or multiple sclerosis.

As used herein, the terra 'immune disorders' refers to the disorders that are associated with the development of particular immune responses, and may be, but not limited to, preferably autoimmune diseases, transplant rejection, graft-versus-host-disease. The autoimmune diseases may be Crohn's disease, erythema, atopic dermatitis, rheumatoid arthritis, Hashimoto's thyroiditis, pernicious anemia, Addison's disease, type 1 diabetes, lupus, chronic fatigue syndrome, fibromyalgia, hypothyroidism and hyperthyroidism, scleroderma, Behcet's disease, inflammatory bowel disease, multiple sclerosis, myasthenia gravis, Meniere's syndrome, Guillain-Barre syndrome, Sjogren's syndrome, vitiligo, endometriosis, psoriasis, vitiligo, systemic scleroderma, asthma, ulcerative colitis or the like.

In the embodiments of the present invention, it was confirmed that the stem cells of the present invention or the culture thereof could treat the inflammatory disease such as colitis and immune disease such as atopic dermatitis in colitis animal models and atopic dermatitis models, suggesting its therapeutic effects on immune disorders and inflammatory diseases.

As used herein, the term 'prevention' means all of the actions in which immune disorders or inflammatory diseases are restrained or retarded by the administration of the composition. As used herein, the term. 'treatment' means all of the actions in which the symptoms of immune disorders or inflammatory diseases are relieved or turned into better condition by the administration of the composition.

Furthermore, the composition of the present invention may include $1.0\times10^5$ to $1.0\times10^9$, preferably $1.0\times10^6$ to $1.0\times10^8$, more preferably $1.0\times10^7$ cells per 1 ml.

The composition of the present invention may be used unfrozen, or frozen for later use. If the population of cells is to be frozen, a standard cryopreservative (e.g., DMSO, glycerol, Epilife® Cell Freezing Medium (Cascade Biologics) is added to the enriched population of cells before it gets frozen.

Furthermore, the composition may be administered by formulating a unit dosage suitable for administering to a patient by conventional methods in the pharmaceutical field, with the formulation containing an effective amount for a single dose or for divided doses. For this purpose, a formulation for parenteral administration preferably includes an injection formulation such as injection ampoule, an infusion formulation such as infusion bag, and spray formulation such as aerosol. The injection ampoule may be mixed with an injection solution such as saline solution, glucose, mannitol and ringer solution immediately before administration of the formulation. Furthermore, the infusion bag may be textured with polyvinyl chloride or polyethylene, for example, a product of Baxter, Becton Dickinson, Medcep, National Hospital Products or Terumo.

The pharmaceutical formulation may further comprise one or more pharmaceutically acceptable inactive carriers, for example, a preservative, an analgesic controller, a solubilizer or a stabilizer for injection formulation, and a base, an excipient, a lubricant or a preservative for topical formulation, in addition to the active ingredient.

The prepared composition or pharmaceutical formulation of the present invention may be administered in accordance with any conventional method in the art together with other stem cells used for transplantation and other purposes, or in the form of a mixture therewith. Direct engraftment or transplantation to the lesion of a patient, in need of treatment, or direct transplantation or injection into the peritoneal cavity is preferred, but is not limited thereto. Furthermore, both of a non-surgical administration using a catheter and a surgical administration such as injection or transplantation after incision are possible, but non-surgical administration using a catheter is core preferred, in addition, the composition can also be administered parenterally, for example, intravenous injection, which is one of the conventional methods for transplantation of stem cells of hematopoietic system, besides direct administration to the lesion.

The stem cells may be adminstered in an amount of $1.0\times10^4$ to $1.0\times10^{10}$ cells/kg (body weight), preferably $1.0\times10^5$ to $1.0\times10^9$ cells/kg (body weight) per day in a single dose or in divided doses. However, it should be understood that the amount of the active ingredient actually administered ought to be determined in light of various relevant factors including the disease to be treated, the condition to be treated, the severity the patient's symptom, the chosen route of administration, and the body weight, age and sex of the individual patient; and, therefore, the above dose should not limit the scope of the invention in any way.

In another aspect, the present invention provides a method for treating immune disorders or inflammatory disease, comprising the step of administering the composition to a subject with immune disorder or inflammatory disease.

In still another aspect, immune responses can be suppressed or inflammation can be regulated by administration of the NOD2 agonist-treated stem cells according to the present invention and the culture thereof, and therefore, the present invention provides a method for suppressing immune responses or inflammatory responses or a subject, which involves the step of administering the stem cells generated by adding the NOD2 agonist to stem cells expressing NOD2 or the culture thereof to the subject.

As used herein, the term 'subject' means a mammal including cattle, dogs, swine, chickens, sheep, horses, and human, but is not limited thereto. In this regard, the method for suppressing immune responses or inflammatory responses may be limited to animals excluding human. Preferably, administration of the stem cells cultured with addition of NOD2 agonist or the culture, thereof may be performed by intra-abdominal or intravenous injection, direct injection into the lesion, or injection into the synovial cavity.

The suppress son of immune responses or inflammatory responses is for prevention or treatment of immune disorders or inflammatory diseases.

In still another aspect, the present invention provides a method for preparing an immunosuppressive drug or an anti-inflammatory drug, which involves the step of culturing stem cells by adding NOD2 agonist to stem cells expressing Nucleotide-binding Oligomerization Domain protein 2 (NOD2).

As used herein, the term 'immunosuppressive drug', as described above, means a drug comprising stem cells generated by culturing stem cells expressing NOD2 with the NOD2 agonist or the culture thereof, which is able to treat immune disorders by suppressing immune responses.

As used herein, the term 'anti-inflammatory drug', as described above, means a drug comprising stem cells generated by culturing stem cells expressing NOD2 with the NOD2 agonist or the culture thereof, which is able to treat inflammatory diseases by suppressing inflammation.

In still another aspect, the present invention provides a method for preparing $PGE_2$ or TGF-β1, which involves the step of culturing stem cells expressing Nucleotide-binding Oligomerization Domain protein 2 (NOD2) in a medium treated with NOD2 agonist, in which prostaglandin $E_2$ ($PGE_2$) or transforming growth factor beta 1 (TGF-β1) is secreted from the stem cells during culturing.

In the embodiments of the preset invention, MDP-treated mesenchymal stem cells were found to promote secretion of $PGE_2$ and TGF-β1 significantly which are known to be applicable in various fields, as compared to mesenchymal stem cells untreated with MDP and mesenchymal stem cells treated with other receptor agonists (DAP, LPS, Pam3CSK4, etc.).

In the present invention, for recovery of $PGE_2$ and TGF-β1, the culture medium of the stem cells is collected, and cells and debris are removed by centrifugation and filtration, thereby leaving the supernatant only.

In still another aspect, the present invention provides a graft comprising the stem cells expressing Nucleotide-binding Oligomerization Domain protein 2 (NOD2) and the NOD2 agonist.

As used herein, the term 'graft' means a material that can be transplanted into human or mammal, which protects the damaged tissue from outside or supports a transplanted cell or secreted therapeutic substance to remain in the same place. The graft is used as a support for tissue engineering and involves biodegradable synthetic polymers and natural materials that are used in the art but is not limited thereto. Since the graft of the present invention comprises the stem cells expressing NOD2 and the NOD2 agonist, there is an advantage in that it does not cause transplant rejection or inflammatory responses. Therefore, without any additional immunosuppressive agent or anti-inflammatory drug needed to suppress transplant rejection or inflammatory responses caused by transplantation of various grafts, the transplanted graft can be stably engrafted on the body without incurring transplant rejection or inflammatory responses.

In still another aspect, the present invention provides a graft that is prepared by culturing the stem cells expressing Nucleotide-binding Oligomerization Domain protein 2 (NOD2) in the graft with a NOD2 agonist, and then removing stem cells therefrom.

in still another aspect, the present invention provides a method for preparing the graft, comprising the step of culturing the stem cells expressing Nucleotide-binding Oligomerization Domain protein 2 (NOD2) in the graft with a NOD2 agonist.

Preferably, the method may further comprises the step of removing stem cells after the culturing step.

In still another aspect, the present invention provides a composite comprising the stem cells expressing Nucleotide binding Oligomerization Domain protein 2 (NOD2) and the NOD2 agonist.

Preferably, the NOD agonist may bind to NOD2 of the stem cells in the composite. More preferably, NOD2 may be activated by binding of the NOD2 agonist to NOD2 of the stem cells in the composite. Ultimately, the composite may be used for cell therapy.

In still another aspect, the present invention provides a culture that is generated by culturing stem cells expressing Nucleotide-binding Oligomerization Domain protein 2 (NOD2) with a NOD2 agonist.

The culture may comprise components such as $PGE_2$ and/ or $TGF-\beta 1$, which exhibit the prophylactic or therapeutic effects on immune, disorders or inflammatory diseases.

Hereinafter, the present invention is described in more detail through providing Examples as below. However, these Examples are merely meant to illustrate, but in no way to limit, the claimed invention.

In the following Examples, only the use of mesenchymal stem cells derived from umbilical cord blood is exemplified, but it is apparent to those skilled in the art from the foregoing description, that the mesenchymal stem cells and stem cells having other NOD2 receptors can be treated with NOD2 agonists for inducing a remarkably increase in the level of $PGE_2$ production in order to get immunosuppressive or anti-inflammatory effects.

Moreover, MDP was used as a NOD2 agonist in the present Examples. However, as shown in the following Examples, the stem cells wherein NOD2 receptors are inhibited have no immune regulatory activity, and thus it will be apparent to those skilled in the art from the foregoing description that even when other NOD2 agonists are used, the immunosuppressive or anti-inflammatory effects of the present invention can be achieved.

EXAMPLE 1

Isolation and Culturing of Human Umbilical Cord Blood-Derived Mesenchymal Stem Cells (Hereinafter, Referred to as hUCB-MSC) and Human Umbilical Cord Blood-Derived Mononuclear Cells (Hereinafter, Referred to as hUCB-MNC)

The Umbilical Cord Blood (UCB) samples were obtained from the umbilical vein immediately after delivery, with the written consent of the mother approved by the Boramae Hospital and the Seoul National University Institutional Review Board (IRB No. 0603/001-002-07C1). The UCB samples were mixed with the Hetasep solution (StemCell Technologies, Vancouver, Canada) in a ratio of 5:1, and then incubated at room temperature to remove erythrocyte. The mononuclear cells were carefully collected by adding Ficoll solution to the sample and centrifuging the mixture at 2500 rpm for 20 minutes separating it from the supernatant. Then the pelleted cells were washed twice with PBS.

The hUCB-derived mononuclear cells (hUCB-MNCs) were cultured in RPMI-1640 medium (Gibco, Grand Island, N.Y., USA) supplemented with 10% fetal bovine serum (FBS).

The hUCB-derived mesenchymal stem cells (hUCB-MSCs) were cultured at a density of $2 \times 10^5 \sim 2 \times 10^6$ cells/cm$^2$ in D-media (Formula No. 78-5470EF, Gibco BRL) which contains EGM-2 SingleQuot and 10% FBS (Gibco BRL). After 3 days of culturing, non-adherent cells were removed. It was observed that the adherent cells formed colonies and grew rapidly, showing spindle-shaped morphology. The mesenchymal stem cells isolated from each of the UCB sample were designated as #618 and #620 respectively.

EXAMPLE 2

Identification of the Receptors Expressed in hUCB-MSC 2-1: Identification of the Expression of Functional TLR2, TLR4, NOD1, and NOD2 in hUCB-MSC RT-PCR was performed to determine whether functional Toll Like Receptor 2 (TLR2), Toll Like Receptor (TLR4), Nucleotide-binding Oligomerization Domain proteins (NOD1) and Nucleotide-binding Oligomerization Domain proteins 2 (NOD2) are expressed in hUCB-MSCs.

To be specific, total RNA was extracted from hUCB-MSCs by using an Easy-spin total RNA extraction kit (Intron Biotechnology, Seongnam, Korea), cDNA was prepared from 1 μg of total RNA by using Superscript III reverse transcriptase (Invitrogen, Carlsbad, Calif., USA) and oligo (dT) primers (Invitrogen). The primer sets used are as follows (F: Forward, R: Reverse).

```
TLR2 F (SEQ ID NO. 1):
5'-GATGCCTACTGGGTGGAGAA-3'

TLR2 R (SEQ ID NO. 2):
5'-CGCAGCTCTCAGATTTACCC-3'

TLR4 F (SEQ ID NO. 3):
5'-ACAGAAGCTGGTGGCTGTG-3'

TLR4 R (SEQ ID NO. 4):
5'-TCTTTAAATGCACCTGGTTGG-3'

NOD1 F (SEQ ID NO. 5):
5'-CCACTTCACAGCTGGAGACA-3'

NOD1 R (SEQ ID NO. 6):
5'-TGAGTGGAAGCAGCATTTTG-3'

NOD2 F (SEQ ID NO. 7):
5'-GAATGTTGGGCACCTCAAGT-3'

NOD2 R (SEQ ID NO. 8):
5'-CAAGGAGCTTAGCCATGGAG-3'

Rip2 F (SEQ ID NO. 9):
5'-CCATTGAGATTTCGCATCCT-3'
```

-continued

Rip2 R (SEQ ID NO. 10):
5'-ATGCGCCACTTTGATAAACC-3'

RPL13A F (SEQ ID NO. 11):
5'-CATCGTGGCTAAACAGGTAC-3'

RPL13A R (SEQ ID NO. 12):
5'-GCACGACCTTGAGGGCAGCC-3'

The PCR condition was set to have an initial denaturation at 95° C. for 3 min; 30 cycles of 94° C. for 30 sec, 60° C. for 30 sec and 72° C. for 1 min; a final extension at 72° C. for 10 min. The PCR products were separated on a 1.5% agarose gel, visualized, and the image of the gel was photographed using a gel documentation system.

As shown in FIG. 1a, in a positive control group containing a human monocytic leukemia cell line, i.e. THP-1 cell, all of the receptors of interest were expressed in both THP-1 cells and hUCB-MSCs. TLR4 was expressed at higher level in hUCB-MSCs than in THP-1 cells, whereas the gene expression levels of TLR2, NOD1, and NOD2 were greater in THP-1 cells. Meanwhile, Rip2 expression was also observed, in hUCB-MSCs.

2-2: Analysis of Cytokine Production in Response to Stimulation by Agonists of the Receptors of Interest After conforming the expression of the receptors of interest in hUCB-MSC in Example 2-1, the functionality of the receptors investigated by monitoring IL-8 production after stimulation by agonists. For this experiment, hUCB-MSCs were cultured at a density of $2 \times 10^4$ cells/well in KSFM medium supplemented with 2% FBS in a 96-well plate. After 24 hours of culturing, the cells were treated with the following agonists corresponding to each of the receptors, i.e., Pam3CSK4 (TLR2 agonist, Pam3), LPS (TLR4 agonist), Tri-DAP (NOD1 agonist, T-DAP), and MDP (NOD2 agonist). Then the samples were incubated for additional 24 hours. The supernatant of each culture was collected, centrifuged, and filtered through a 0.2 μm filter. Then, concentrations of IL-8 and $PGE_2$ were measured using an ELISA kit (R&D Systems, Minneapolis, Minn., USA). Ultrapure LPS (*E. coli* O111: B4), Pam3CSK4, and Tri-DAP were purchased from Invivogen (San Diego, Calif., USA), MDP [Ac-(6-O-stearoyl)-muramyl-Ala-D-Glu-NH2; muramyl dipeptide] was purchased from Bachem (Bubendorf, Switzerland). Recombinant human Interferon-γ was purchased from Peprotech (Rockyhill, N.J., USA).

Figure 1B:
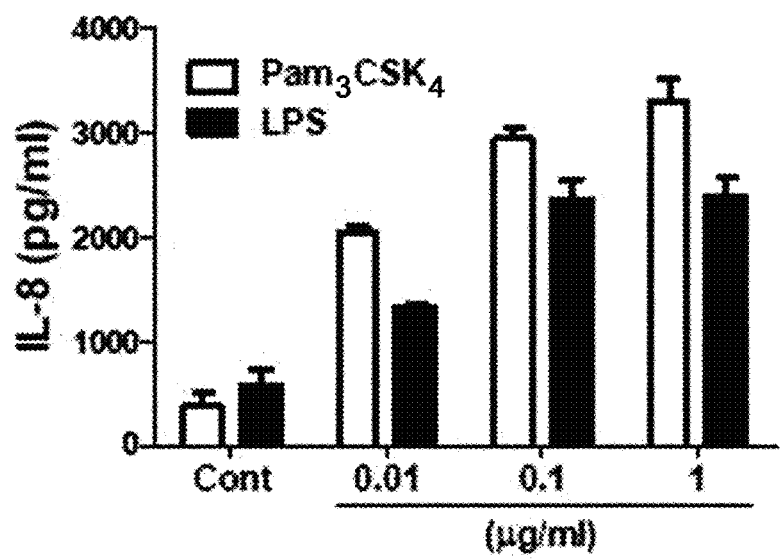
FIGS. 1b to 1e show the level of IL-8 expression and MSC proliferation after treatment with each agonist.
Figure 1C:
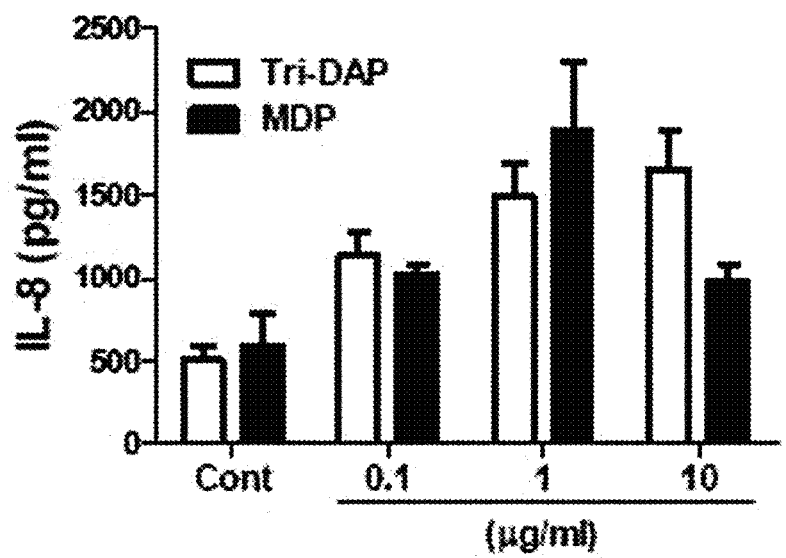

As shown in FIGS. 1b and 1c, stimulation by Pam3CSK4 (Tri-acylated peptide; TLR2 agonist), LPS (Lipopolysaccharide, TLR4 agonist), Tri-DAP (Tri-diaminopimelic Acid, NOD1 agonist), and MDP (NOD2 agonist) led to the increased IL-8 production in hUCB-MSCs in a dose-dependent manner. These results suggest that NOD1, NOD2, TLR2 and TLR4 are expressed and actively respond to the stimulation by agonists in hUCB-MSCs.

2-3: Analysis of the Effects of TLR and NLR Stimulation by Agonists on hUCB-MSC Proliferation (1)

Based on the previous finding that a certain type of MSC is affected by TLR stimulation (Pavsner-Ficher et al., Toll-like receptors and their ligands control mesenchymal stem cell functions, Blood, 109:1422, 2007), the effect of agonists on hUCB-MSC proliferation was investigated by treating the cells with each of the agonists, and culturing them for 4 days.

More particularly, cells were cultured at a density of $2 \times 10^3$ cells/well in MSC medium supplemented with 2% FBS in a plate. After 24 hours of culturing, the cells were treated with Pam3CSK4 (TLR2 agonist), LPS (TLR4 agonist), Tri-DAP (NOD1 agonist) and MDP (NOD2 agonist) at a concentration of 10 μg/ml each and then cultured for 4 more days. Cell proliferation was monitored by using Cell Counting Kit-8 (Dojindo Molecular Technologies, Rockville, Md., USA). The difference in results for each type of experimental groups was represented by standard deviation (±SD). All statistical analysis was performed using MS Excel program, and test values of p<0.05 were regarded as statistically significant (hereinafter, the same).

Figure 1D:
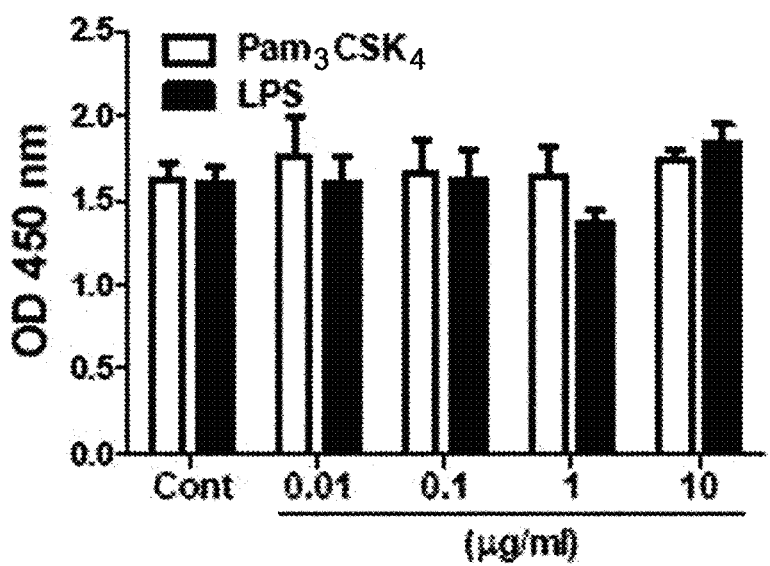
Figure 1E:
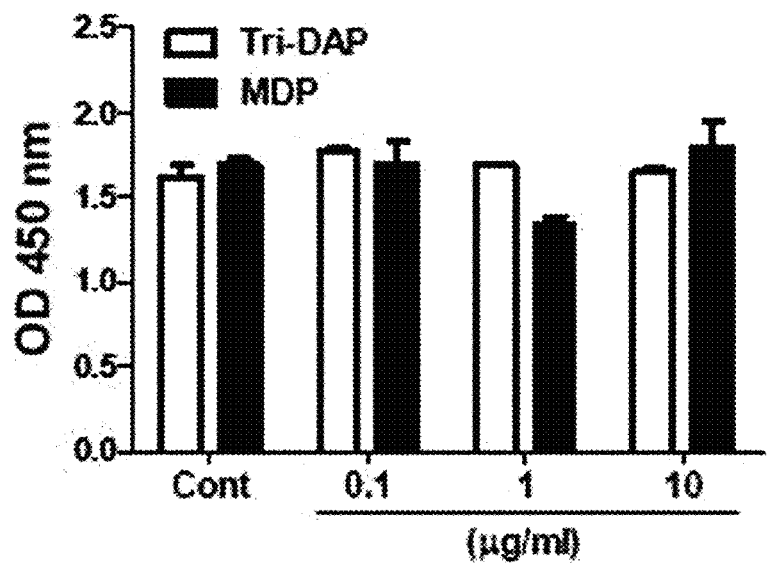

As shown in FIGS. 1d and 1e, none, of the agonists were found to have an effect on proliferation of hUCB-MSC.

2-4: Analysis of the Effects of TLR and NLR Stimulation by Agonists on the Suppressive Activity of hUCB-MSC Against Human MNC Proliferation (2)

In the present experiment, the inventors investigated whether TLR and NLR agonists enhance the suppressive activity of hUCB-MSC against human NEC proliferation.

Figure 2:
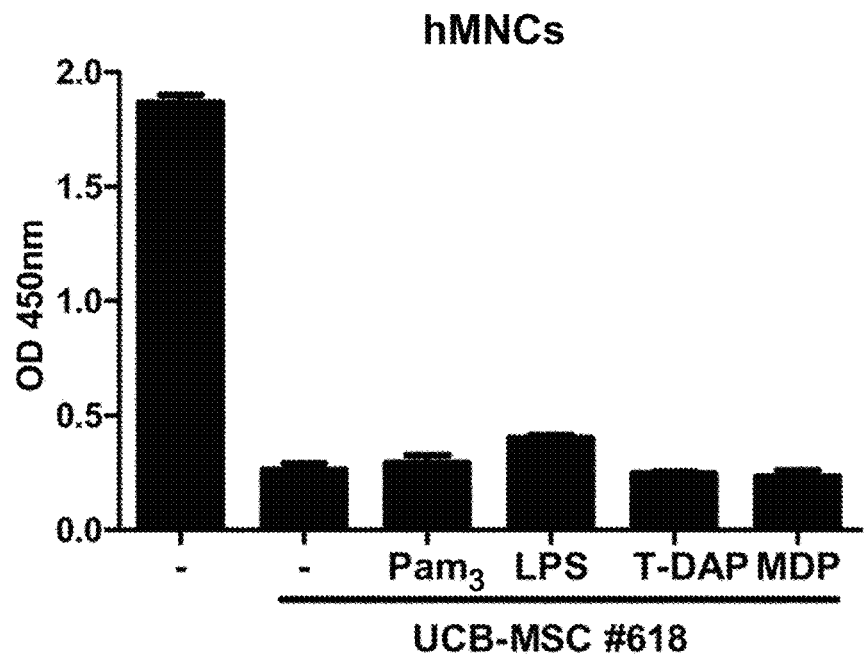
FIG. 2 is a graph showing the effect of hUCB-MSC on MNC proliferation after treatment with each agonist.

Based on the study that identified the importance of a direct interact ion between MSCs and lymphocytes in inhibition of lymphocyte proliferation by MSCs, the present inventors investigated whether MDP has an effect on the suppressive ability of hUCB-MSCs against MNC proliferation under the conditions where two cell groups are in contact with each other.

shown in FIG. 2, hUCB-MSCs (#618) drastically inhibited the proliferation of human MNCs under direct cell to cell interaction. However, TLR (Pam3CSK4 and LPS) agonists and NLR agonists (Tri-DAP and MDP) did not affect the suppressive activity of hUCB-MSCs against MNC proliferation under the same condition (FIG. 2).

EXAMPLE 3

Identification the Enhanced Immunosuppressive Activity of hUCB-MSC by MDP Through NOD2-Rip2 Dependent Pathway (1)

3-1: Determination of the Effect of Secretory Factor Generated from MDP-Treated hUCB-MSC on MNC Proliferation Soluble factors are also known to mediate immunosuppression by MSC. So the present inventors examined whether secretory factors generated by UCB-MSCs have an effect on human MNC proliferation. Culture medium (CM) was prepared, and hUCB-MSCs were co-cultured with the agonist for 24 hours. After washing, the cells were cultured fresh for additional 4 is. Then, a control group containing culture medium (CM) and sample of hUCB-MSCs treated with agonist (#613) were prepared, and MNCs were cultured in CM containing hUCB-MSCs for 3 days.

Figure 3A:
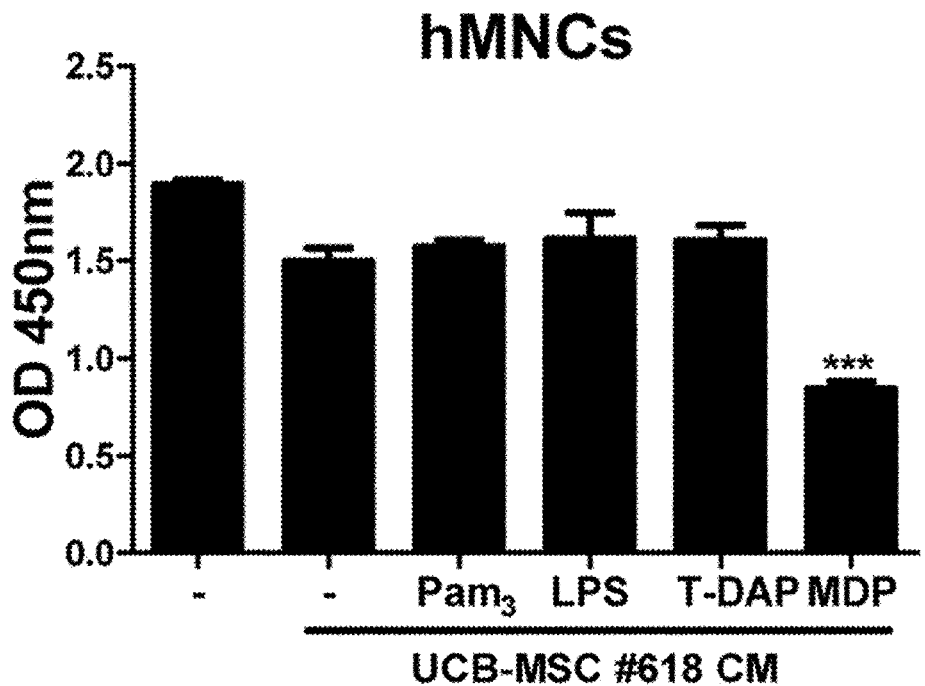
FIG. 3 is a graph showing the effect of hUCB-MSC culture on MNC proliferation (3a and 3b) and splenocyte proliferation (3c) after treatment with each agonist.
Figure 3B:
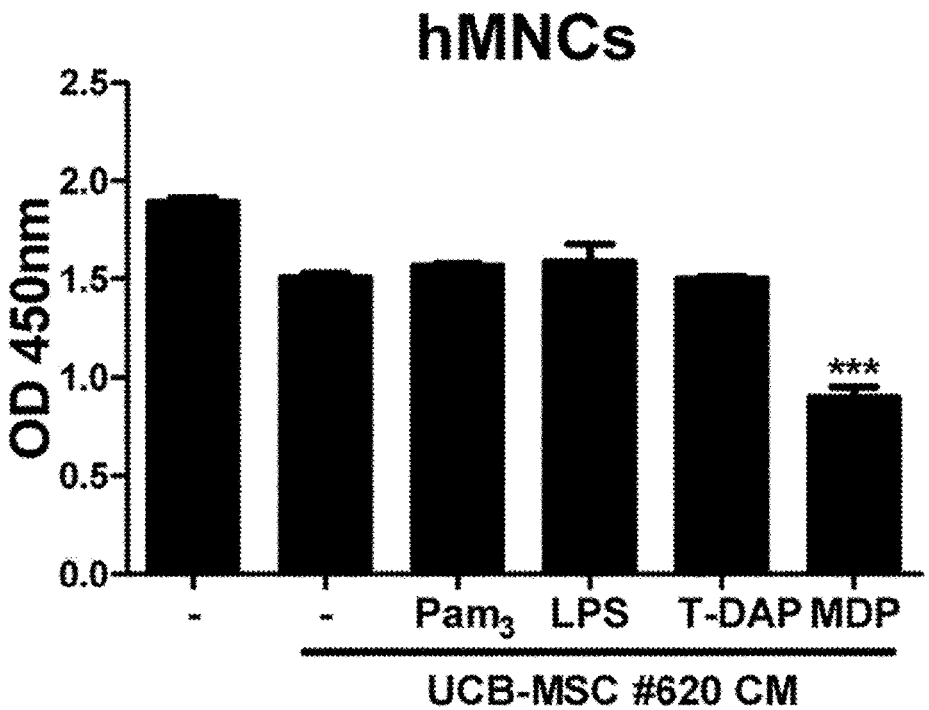
Figure 3C:
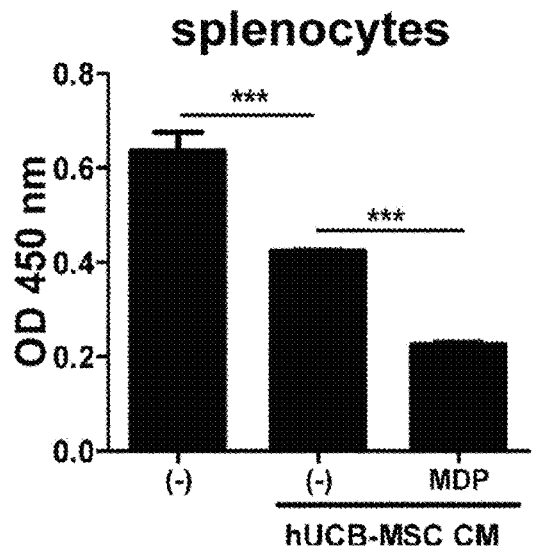

The experimental results demonstrated that MNC proliferation was slightly inhibited in the control group containing hUCB-MSC culture medium (UCM) (FIG. 3a). Surprisingly, when the MNCs were cultured in UCM that was pre-treated with MDP (MDP-UCM), MNC proliferation was inhibited at greater level, but this effect was absent when other agonists were used to treat UCM (Pam3CSK4, LPS, Tri-DAP) (FIG. 3a). The similar results were observed when UCM prepared from other sample of hUCB-MSCs (#620) was used (FIG. 3b). Furthermore, proliferation or xenogeneic mouse splenocytes was also inhibited when they were cultured in the presence of UCM, and this inhibitory effect was enhanced by MDP stimulation (FIG. 3c). These results suggest that secretory factors from MDP-treated hUCB-MSCs play an important role in immunosuppression of MNC.

3-2: Identification of the Enhanced Immunosuppressive Activity of hUCB-MSC by MDP Treatment To determine whether MDP enhances the immunosuppressive activity of in UCB-MSC, the following experiment was performed. A control group containing culture medium (CM) of hUCB-MSC was prepared and the agonist-treated hUCB-MSCs were collected on the 5$^{th}$ day of culturing. Then, MNC was co-cultured in CM of hUCB-MSC for 3 days more, and after culturing, the level of MNC proliferation was monitored.

Figure 4:
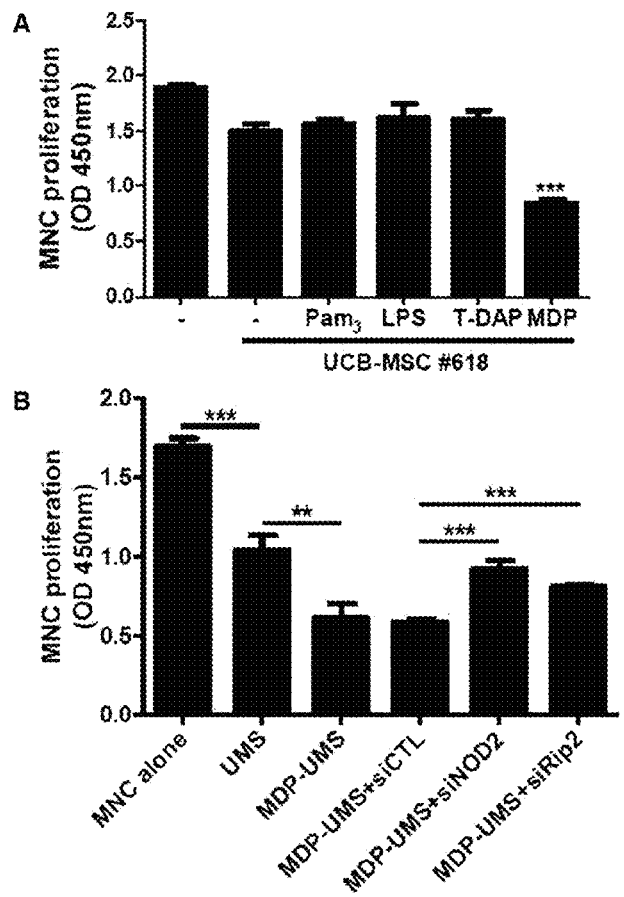
FIG. 4 shows the comparison of the inhibitory effect of mesenchymal stem cell (hUCB-MSC #618) culture treated with MDP alone (A) and the result of siRNA treatment (B)

As shown in FIG. 4A, MNC proliferation was significantly inhibited in the supernatant of mesenchymal stem cells that were treated with the agonist MDP (UCB-MSC #618+MDP) compared to the untreated UCB-MSC supernatant (UCB-MSC #618).

On the other hand, the rate of MNC inhibition was similar in between the supernatants of mesenchymal stem cells that were treated with other agonists (LPS, etc.) (UCB-MSC #618+Pam3; UCB-MSC #618+LPS; UCB-MSC #618+T-DAP) and the untreated UCB-MSC supernatant (UCB-MSC 618). That is, compared to the untreated negative control group, the proliferation of MNC group was only slightly inhibited when treated with other agonist.

These results suggest that MNC proliferation is remarkably inhibited by soluble factors secreted from MDP-treated mesenchymal stem cells.

3-3: Investigation of the Correlation Among NOD2, Rip2 and MDP in MNC Inhibition by Using siRNA of NOD2 and Rip2

Additionally, to investigate the correlation among NOD2, Rip2 and MDP in MNC inhibition, the following experiment was conducted using siRNAs of 11002 and Rip2 and a control group (siCTL). When the cell density reached 60%, siRNAs were transfected into the cells. The siRIPK2 (M-003602-02) which is the siRNA of receptor-interacting serine-threonine kinase 2 (RIPK2 or receptor interacting kinase protein 2 (Rip2) which is the adaptor of 11001 and NOD2 and the type of kinase called RICK or CARDIAK (Bertin et al, 1999; Inohara et al, 1999; Ogura et al, 2001b)), siNOD2 (J-011338-07) which is the siRNA of NOD2, and a non-targeting control (siControl #1, D-001810-01) were purchased from Dharmacon (Chicago, Ill., USA). DharmaFECT1 (Dharmacon) was used as a transfection reagent, and siRNA was transfected at a concentration of 100 nmol/L. About 48 hours later, the medium was replaced with the fresh one, and the cells were treated with 10 µg/mL of MDP (NOD2 agonist) for 24 hours, except for a negative control (culture medium of MNC only) and a positive control (medium added with UCB-MSC supernatant (UMS) without agonist).

That is, a medium where MNC was cultured alone (i), and a medium added with UCB-MSC supernatant (UMS) without agonist (ii) were prepared as control groups, and a medium treated with MDP and UMS (iii), a medium treated with MDP, UMS, and control siRNA (siCTL) (iv), a medium treated with MDP, UMS and siNOD2 (v), and a medium treated with MDP, UMS, and siRip2 (vi) were prepared. Thereafter, MNC proliferation was measured by optical density at the wavelength of 450 nm.

As shown in FIG. 4B, the rate of MNC proliferation inhibition was similar in medium (iv) and medium (iii), whereas the rate of MNC proliferation inhibition in media (v) and (vi) was similar to that of medium (ii). In other words, the siRNAs of NOD2 and Rip2 could counteract the effect of MDP in enhancing the inhibition of MNC proliferation, but the control sRNA did show the above effect. These results indicate that NOD2 and Rip2 positively regulate MDP-induced immune responses. Therefore, it is suggested that NOD2 and Rip2 are required for MDP-regulated-UCB-MNC inhibition.

EXAMPLE 4

Identification of the Enhanced Immunosuppressive Activity of hUCB-MSCs by MDP Through NOD2-Rip2 Dependent Pathway (2)

Figure 5:
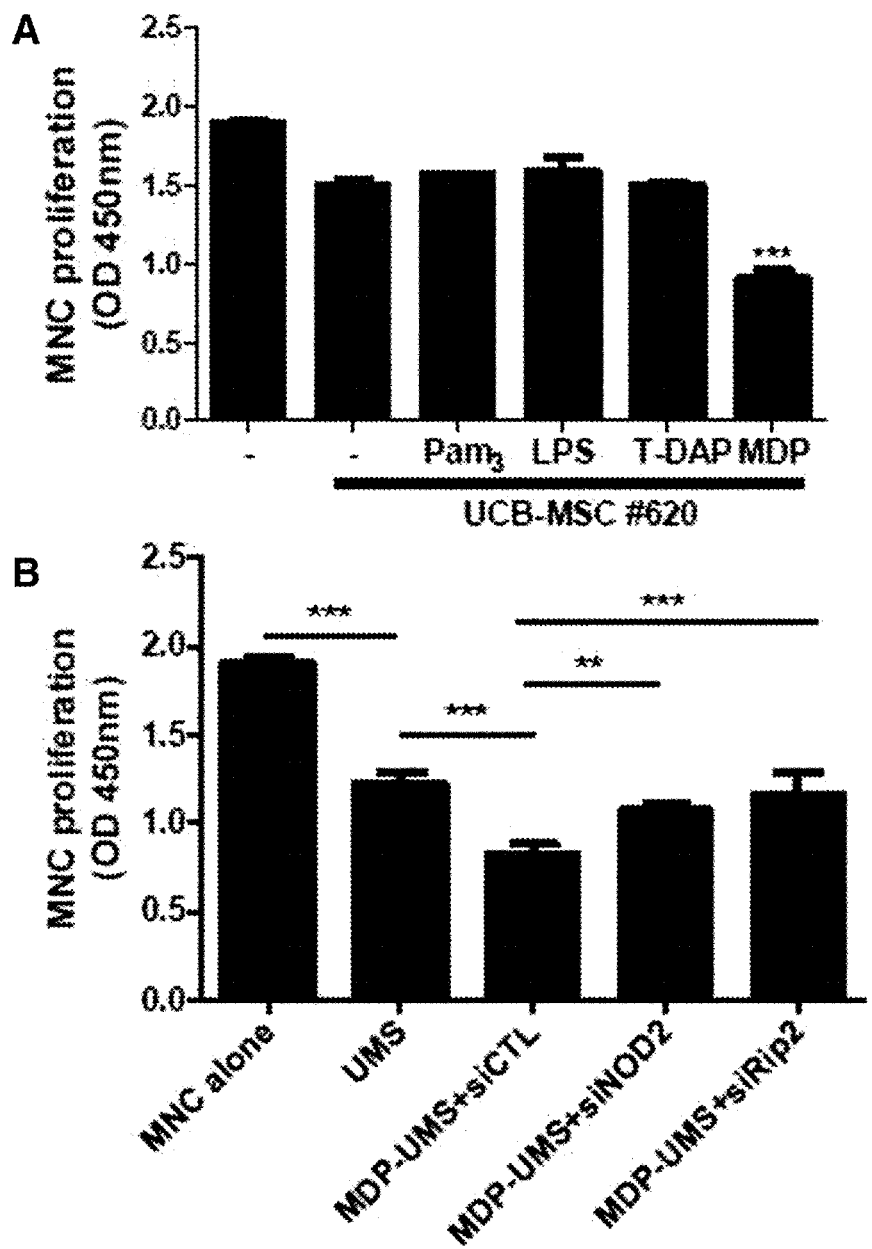
FIG. 5 shows the comparison of the inhibitory effect of mesenchymal stem cell (hUCB-MSC #620) culture treated with MDP alone (A) and the result of siRNA treatment (B)

In order to verify the experimental results in Example 3, the mesenchymal stem cell line #620 obtained from Example 1 was used to perform the experiment following the same method described in Examples 3-2 and 3-3.

shown in FIG. 5A, in the agonist MDP-treated mesenchymal stem cell supernatant (UCB-MSC #618+MDP) MNC proliferation was remarkably inhibited as compared to the UCB-MSC supernatant cultured with other receptor agonists or cultured without any agonist (UCB-MSC #620), which are the similar results as observed in Example 3-1. As shown in FIG. 5B, the effect of MDP in enhancing MNC inhibition was counteracted by siRNAs of NOD2 an Rip2, but not by the control siRNA which is also similar to the results of Example 3-3. These results indicate that MDP enhances suppressive activity of mesenchymal stem cells against MNC proliferation via NOD2-Rip2-dependent pathway.

Together with the results of Example 3, the above results suggest that the MDP-treated stem cells of the present invention and the culture thereof demonstrate strong immunosuppressive effects, and thus can be used as an immunoregulatory composition for the treatment of autoimmune diseases such as rheumatoid arthritis and Crohn's disease or immune disorders such as atopic dermatitis.

EXAMPLE 5

Analysis of the Correlation Between MDP-Induced PGE$_2$ Production and MNC Inhibition by UMS (UCB-MSC Supernatant; UMS)

5-4: Increase in PGE$_2$ Secretion from MSC by MDP Stimulation

The hUCB-MSCs (2×10$^4$ cells/well) were cultured in MSC medium supplemented with 2% FBS in a 96-well plate. After 24 hrs of culturing, the cells were treated with 1 µg/mL Pam3CSK4 (TLR2 agonist), 1 µg/mL LPS (TLR4 agonist), 10 µg/mL Tri-DAP (NOD1 agonist) or 10 µg/mL MDP (NOD2 agonist) and cultured for additional 24 hours, then the culture supernatant of each sample was collected. After centrifugation, the culture supernatants were filtered through a 0.2 µm filter. Then, PGE$_2$ concentration was measured using an ELISA kit (R&D Systems, Minneapolis, Minn., USA) following the manufacture's protocol.

Figure 6A:
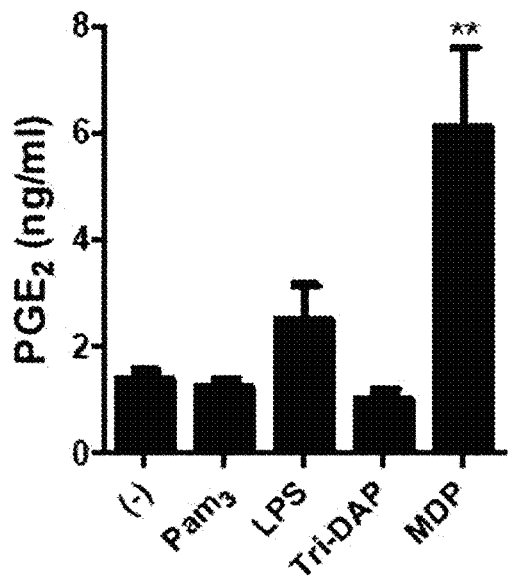
FIG. 6a shows the amount of $PGE_2$ secretion after treatment of each receptor with corresponding agonist.

As shown in FIG. 6a, treatment of hUCB-MSCs with the NOD2 agonist, MDP, significantly enhanced PGE$_2$ secretion, as compared to those treated with the agonists of other receptors.

5-2: Analysis of the Correlation Between COX-2 Expression and MDP Treatment

Cells were treated with 1 µg/mL Pam3CSK4 (TLR2 agonist), 1 µg/mL LPS (TLR4 agonist), 10 µg/mL Tri-DAP (NOD1 agonist) or 10 µg/mL MDP (NOD2 agonist) and cultured for 24 hours. Then, the collected cells were lysed using 1% Nonidet-P40 buffer containing 2 mM dithiothreitol and protease cocktail (Roche, US). The cell lysates were resolved by 12% SDS-PAGE, and transferred onto a nitrocellulose membrane. Then, immunostaining was performed using primary antibodies (COX-2, GAPDH (Santa Cruz biotechnology, Santa Cruz, Calif., USA)). Thereafter, immunostaining was performed using secondary antibodies, and proteins were detected using an enhanced chemiluminescence (ECL) reagent (Intron Biotechnology).

Figure 6B:
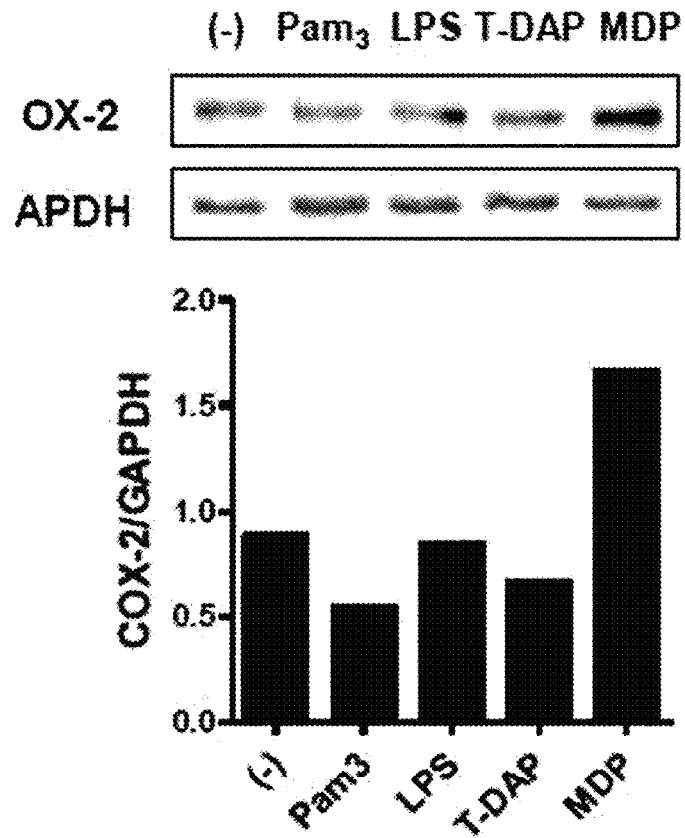
FIG. 6b shows the level of COX-2 expression after treatment of each receptor with corresponding agonist.

As shown in FIG. 6b, hUCB-MSCs treated with the NOD2 agonist, MDP, showed an enhanced COX-2 expression, as compared to those treated with the agonists of other receptors.

5-3: Analysis of the Correlation Between COX-2 Expression and the Activity of NOD2 and Rip2 Stimulated by MDP Treatment To investigate a correlation between COX-2 expression and the function of NOD2 and Rip2, cells were first treated with MDP and further treated with siNOD2 and siRip2. Then the COX-2 expression level was examined. Protein expression level was measured by using the method described in Example 5-2, and the method for siRNA treatment was the same as described in Example 3-3.

Figure 6C:
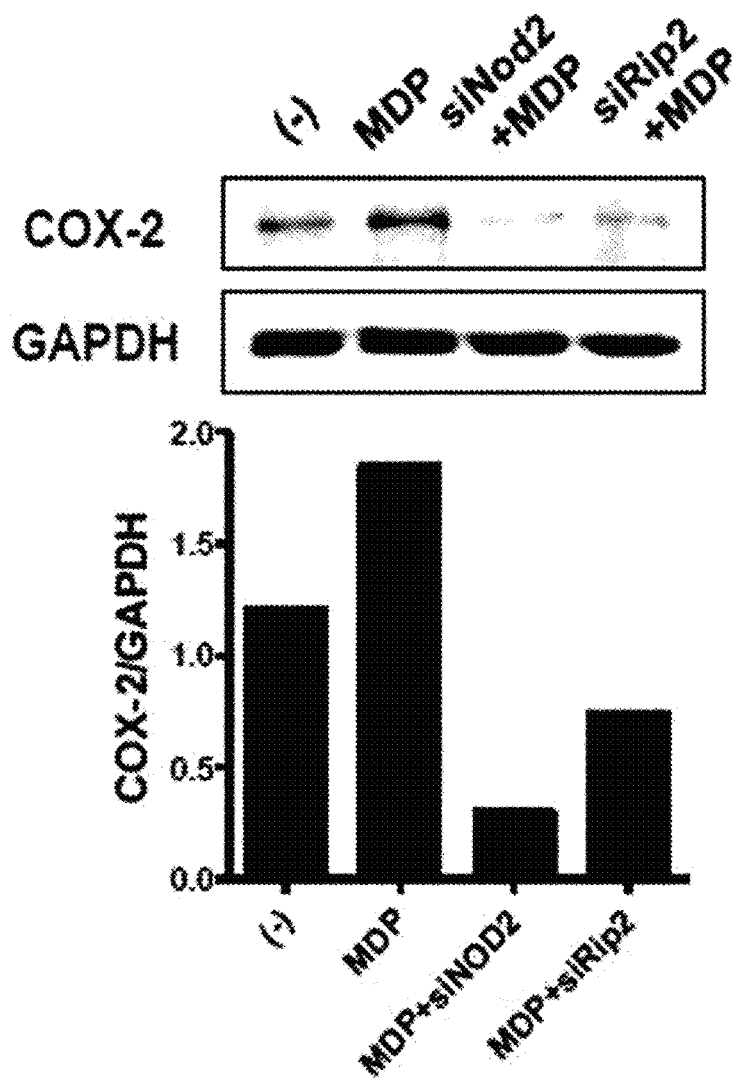
FIG. 6c shows the changes in COX-2 expression level which is increased by treatment of siNOD2 and siRip2 with MDP.

As shown in FIG. 6c, COX-2 expression level was reduced by inhibition of NOD2 and Rip2. This result suggests that COX-2 expression depends on the activity of NOD2 and Rip2.

5-4: Investigation of the Effects of NOD2, Rip2 and COX-2 on $PGE_2$ Expression

To determine the sustainment time of the effects of MDP treatment, the amount of $PEG_2$ produced was monitored after 1 day-long treatment of hUCB-MSCs with MDP. In this experiment, MDP was removed after 1 day of culturing by removing the culture medium and washing the cells with phosphate buffered saline (PBS) 5 times. Then the amount of $PEG_2$ produced was measured. Meanwhile, cells were treated with MDP by the same method described in Example 5-1, and $PGE_2$ concentration was measured. Also, in order to determine the effects of NOD2, Rip2 and COX-2 on $PGE_2$ expression, the cells were treated with each of the control group of Example 3-3 i.e. siRNA (siCTL), siNOD2, siRip2 and COX-2 inhibitor called indomethacin (Sigma (St. Louis, Mo., USA).

Figure 6D:
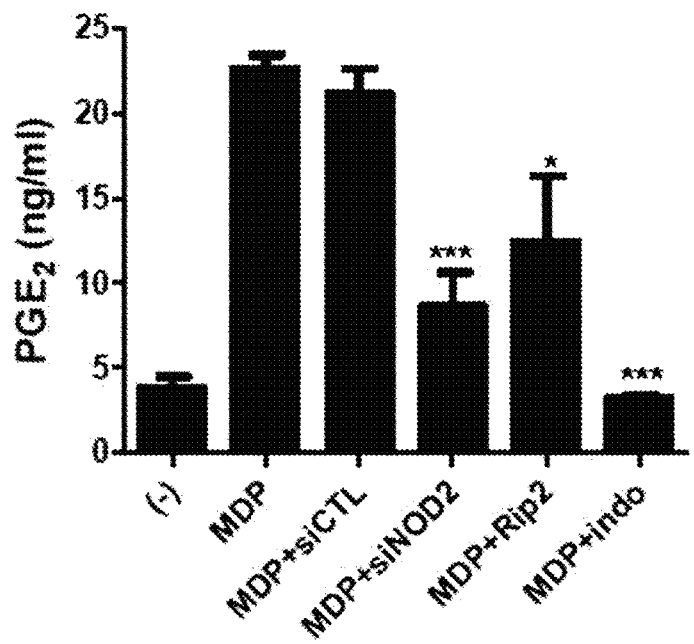
FIG. 6d shows the changes in the amount of $PGE_2$, secretion which is increased by treatment of siNOD2, siRip2 and indomethacin (indo) with MDP.

As shown in FIG. 6d, even when MDP was removed after 1 day of treatment, $PGE_2$ production level in the MDP-stimulated hUCB-MSCs was greater than that in the control group on the 5th day of culturing. In addition, MDP-enhanced $PGE_2$ production was inhibited by transfection with the NOD2 and Rip2 siRNAs or by inhibition of COX-2 by adding indomethacin. These results indicate that NOD2, Rip2 and COX-2 take an important role in MDP-induced $PGE_2$ production in hUCB-MSCs.

5-5: Investigation of the Role of $PGE_2$ in Inhibition of MNC by hUCB-MSC

In order to investigate the role of $PGE_2$ in inhibition of MNC by hUCB-MSC, MNC proliferation was examined when treated with the MSC supernatant, MDP-treated MSC supernatant, and MDP and indomethacin (COX-2 inhibitor)-treated MSC supernatant. The experiment was performed by the same method described in Example 3.

Figure 6E:
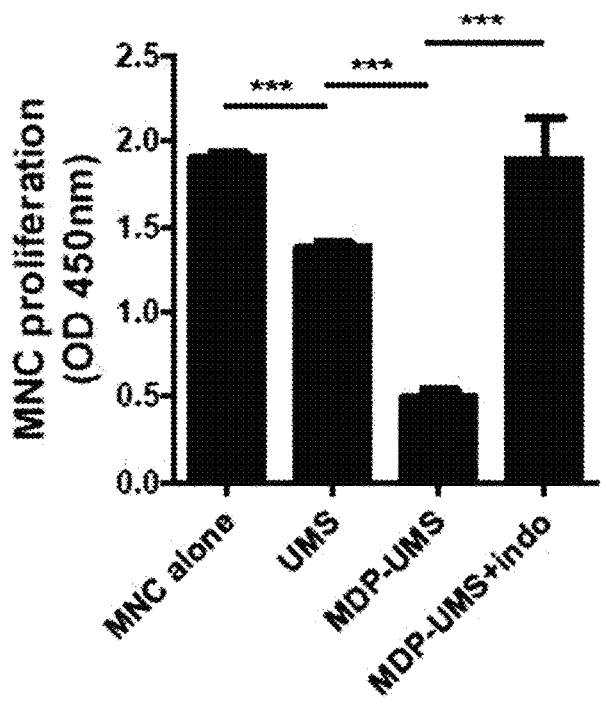
FIG. 6e shows the changes in the inhibitory effect on MNC proliferation, which is increased by treatment of indomethacin (into) with MDP.

As shown in FIG. 6e, cell treatment with the MDP-treated MSC culture medium significantly inhibited MNC proliferation, but co-treatment with indomethacin (Indo) showed MNC proliferation rate similar to that of the negative control group. These results indicate that $PGE_2$ takes an important role in the inhibition of MNC by hUCB-MSC, which is consistent with the result of Example 5-4.

These results suggest that the MDP-treated stem cells of the present invention and the culture thereof produce $PGE_2$ which can be used as an immunoregulatory composition. As aforementioned, since $PGE_2$ is known to inhibit secretion of cytokines such as interleukin-1 beta and TNF alpha, the MDP-treated stem cells of the present invention and the culture thereof can also be used as an anti-inflammatory composition.

5-6: Investigation of the Effect of NOD2 and COX-2 on MDP-Induced Production of Anti-Inflammatory Cytokine Interleukin-10 (IL-10)

In order to determine the production level of IL-10, hUCB-MSCs ($1\times10^5$ cells/well) were cultured in MSC medium supplemented with 2% FBS in a 24 well plate. About 24 hours later, the cells were treated with siNOD2 or indomethacin (Indo), and further cultured for 24 hours. Then the cells were washed five times, and fresh RPMI was added. After 5 days of culturing, UCB-MSC supernatant (UMS) was obtained. MNCs ($1\times10^6$/well) were cultured with UMS and ConA (Sigma (St. Louis Mo., USA)). After 3 days of culturing, cell supernatant was collected, centrifuged, and filtered through a 0.2 μm filter. Then, IL-10 concentration was measured using an ELISA kit (R&D Systems, Minneapolis, Minn., USA).

Figure 6F:
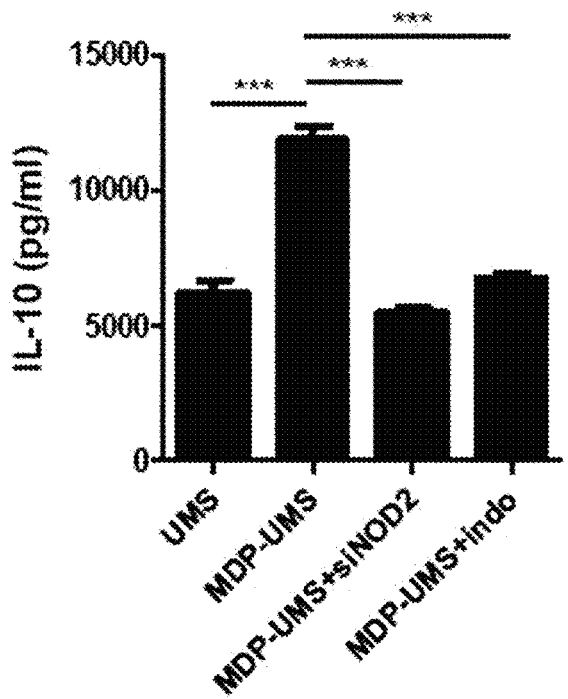
FIG. 6f shows the reduction in the amount of $PGE_2$ secretion which enhanced by treatment of siNOD2 and indomethacin (indo) with MDP.

As shown in FIG. 6f, production of the anti-inflammatory cytokine, IL-10, was remarkably increased by MDP treatment. However, IL-10 production was suppressed by inhibition of NOD2 or indomethacin treatment. These results suggest that MDP treatment increases the production of the anti-inflammatory cytokine IL-10 by acting on NOD2-Rip2 pathway, in which is the same pathway involved in production of $PGE_2$.

In other words, the MDP-treated stem cells of the present invention produce anti-inflammatory cytokine IL-10 at high yield, and thus the MDP-treated stem cells or the culture thereof can be used as an anti-inflammatory composition, in particular, for the treatment of arthritis or the like.

EXAMPLE 6

Analysis of the Correlation Between MNC Inhibition and MDP-Induced Production of $PGE_2$ and TGF-β in hUCB-MSCs 6-1: Investigation of the Effect of MDP on the Production of $PGE_2$ and TGF-β1 in MSC and the COX-2 Expression Soluble factors such as hepatocyte growth factor, TGF-β1, indoleamine 2,3 dioxygenase-1 (IDO-1), nitric oxide (NO), and prostaglandin $E_2$ ($PGE_2$) are the strong candidates for regulating immunosuppression by MSC. In order to determine whether TLR and NLR agonists induce the production of soluble factors including NO, $PGE_2$ and TGF-β1 in hUCB-MSCs, the cells were cultured with Pam3CSK4, LPS, Tri-DAP, and MDP for 24 hours, and culture supernatants were collected. Secretion of the soluble factors was monitored by the method described in Examples 5-1 and 5-2.

Figure 7A:
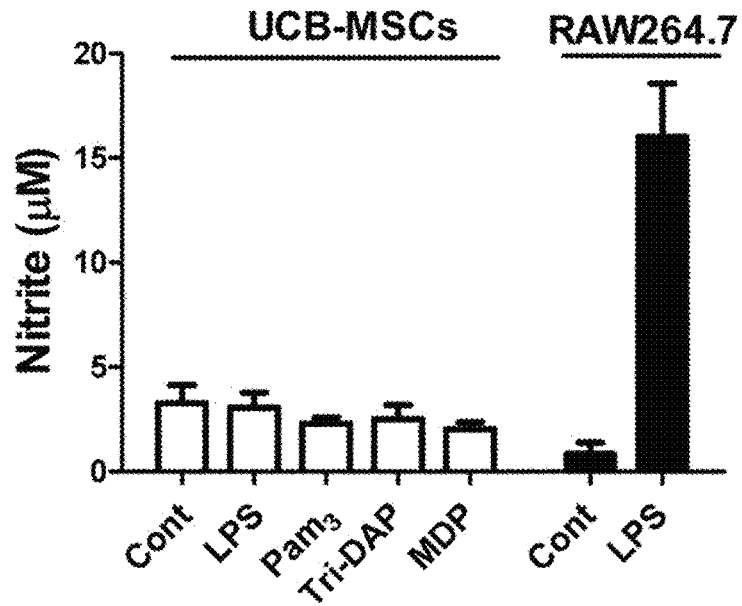
FIG. 7a shows the amount of NO production after treatment of each receptor with corresponding agonist.
Figure 7B:
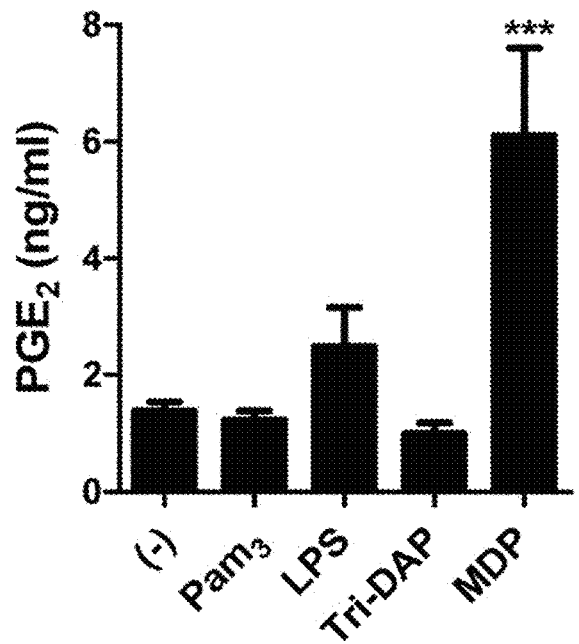
FIG. 7b shows the amount of $PGE_2$ secretion after treatment of each receptor with corresponding agonist.
Figure 7C:
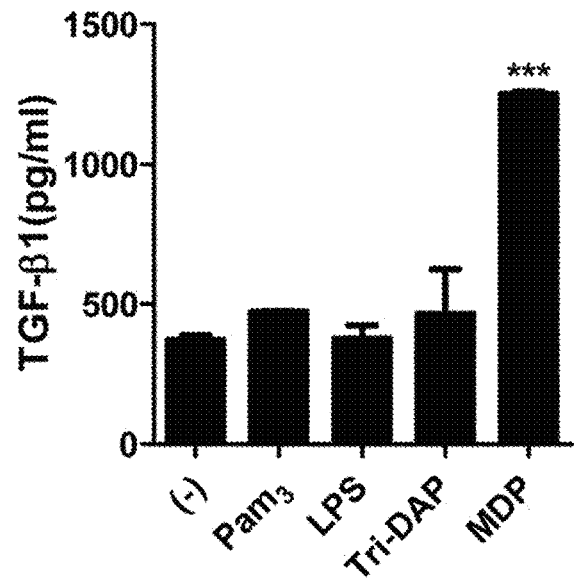
FIG. 7c shows the amount of TGF-β1 secretion after treatment of each receptor with corresponding agonist.
Figure 7D:
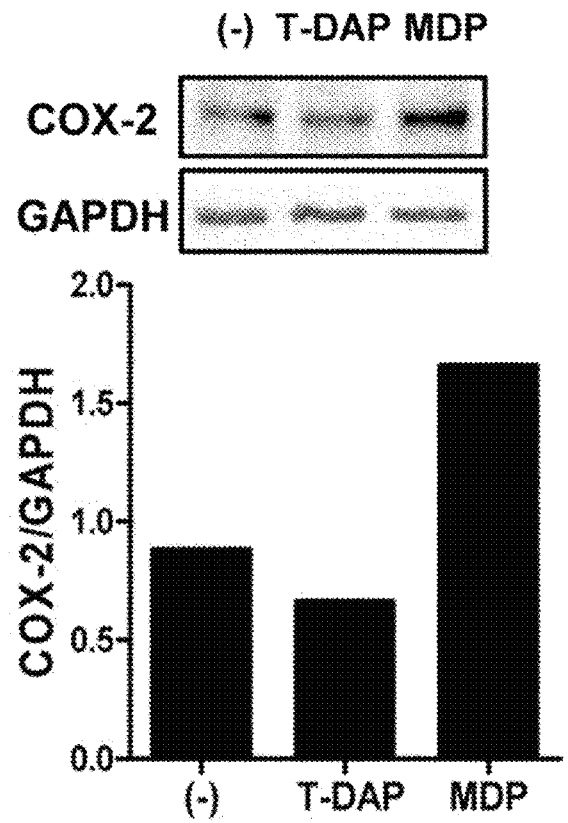
FIG. 7d shows change in the COX-2 expression level after treatment of each receptor with corresponding agonist.

The results demonstrate that single treatment with TLR and NOD agonists did not induce the production of NO in hUCB-MSCs, even though LPS induced the production of NO in macrophages (FIG. 7a). Interestingly, the production of $PGE_2$ and TGF-β1 was enhanced only by addition of MDP in hUCB-MSCs but not by other agonists (FIGS. 7b and 7c). Moreover, expression of COX-2, the $PGE_2$-producing enzyme, was increased in hUCB-MSCs after 24 hours of MDP treatment (FIG. 7d).

6-2: Investigation of the Effect of $PGE_2$ and TGF-β on MNC Proliferation

In order to investigate the effect of $PGE_2$ on mononuclear cell (MNC) proliferation, hMNC and mouse splenocytes were cultured with various concentrations of $PGE_2$. The experiment was performed by the same method described in Example 5-5.

Figure 7E:
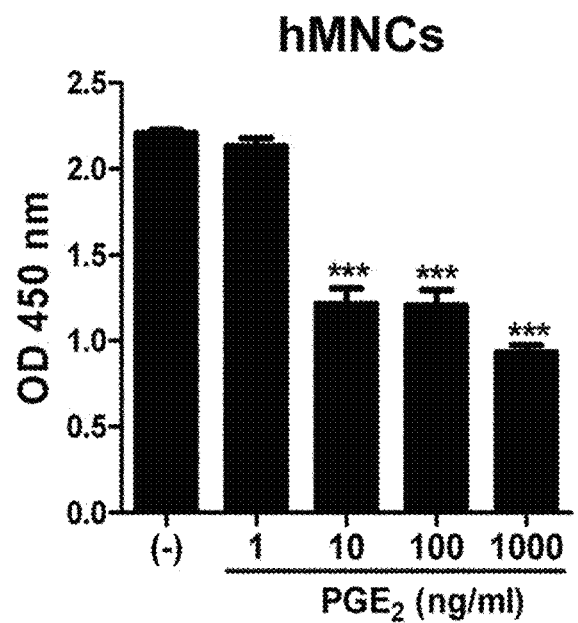
FIG. 7e shows inhibitory effect on MNC proliferation in the presence of PGE$_2$.
Figure 7F:
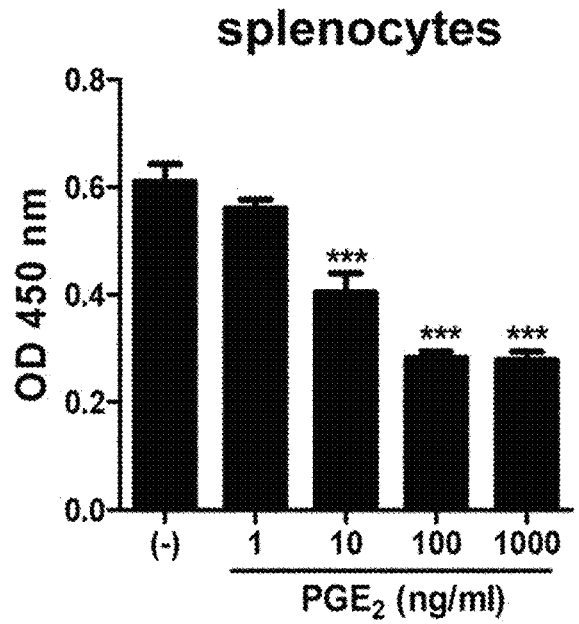
FIG. 7f shows inhibitory effect on splenocyte proliferation in the presence of PGE$_2$.

The results showed that proliferation of hMNC and mouse splenocytes was remarkably inhibited when cultured with $PGE_2$ at a concentration of 10 ng/mL or higher (FIGS. 7e and 7f).

Next, the present inventors examined whether hMNC inhibition by MDP-pretreated UCM is attributed to $PGE_2$ and TGF-β1. The experiment was performed by the same method described in Example 5-5.

Figure 7G:
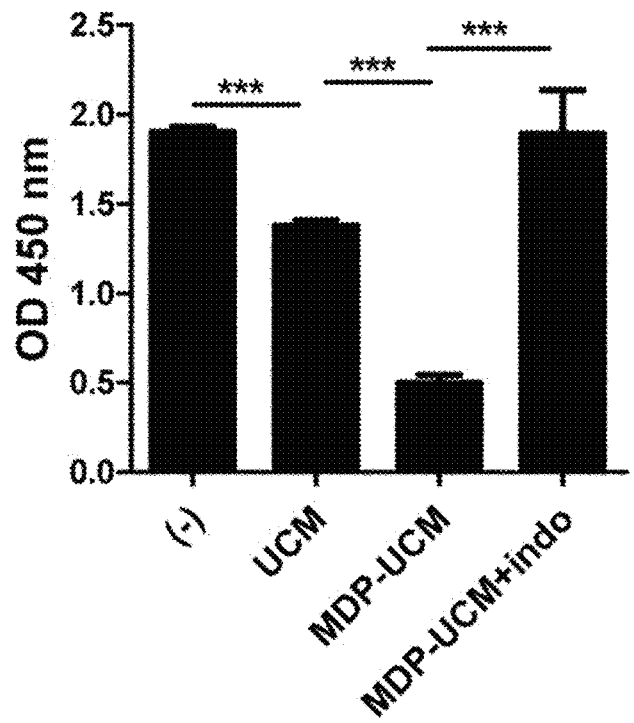
FIG. 7g shows inhibitory effect on MNC proliferation, which is enhanced by treatment of indomethacin (indo) with MDP.
Figure 7H:
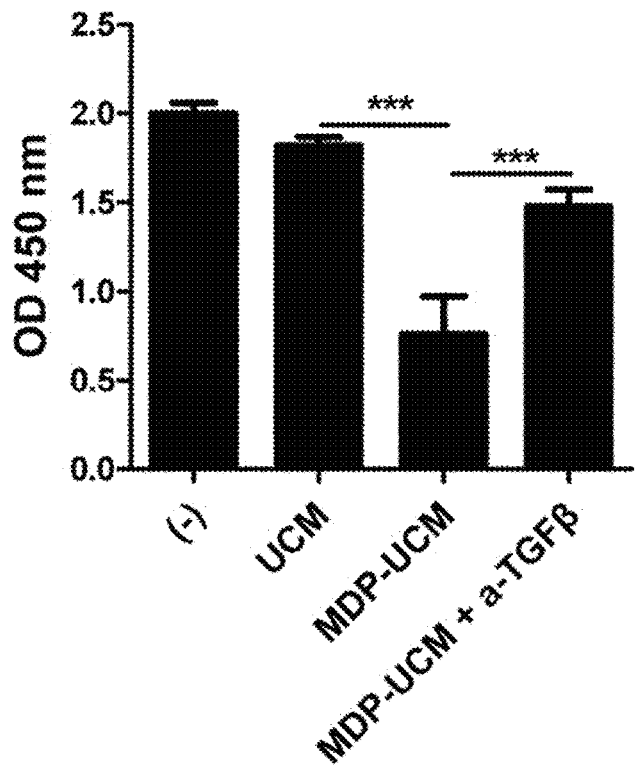
FIG. 7h shows inhibitory effect on MNC proliferation, which is improved by treatment of TGF-β1 neutralizing antibody (a-TGF-β1) with MDP.

The results showed that the inhibitory effect of MDP-UCM on hMNC proliferation was counteracted by a COX inhibitor indomethacin (FIG. 7g). Furthermore, when co-treated with TGF-β1 neutralizing antibody, MDP-UCM did not inhibit hMNC proliferation (FIG. 7h). These results suggest that MDP induces the production of $PGE_2$ and TGF-β1 in hUCB-MSCs, which mediates the immunosuppressive activity of hUCB-MSCs.

EXAMPLE 7

Analysis of the Correlation Between the MDP-Induced COX-2 Expression and $PGE_2$ and TGF-β1 Production in hUCB-MSCs and the Activity of NOD2 and Rip2

NOD2 and Rip2 are the important factors in MDP-induced immune responses. Therefore, the present inventors examined whether NOD2 and Rip2 are required in the MDP-induced COX-2 expression and production of $PGE_2$ and TGF-β1 in hUCB-MSCs. The experiment was performed by the same method described in Example 5-4.

Figure 8:
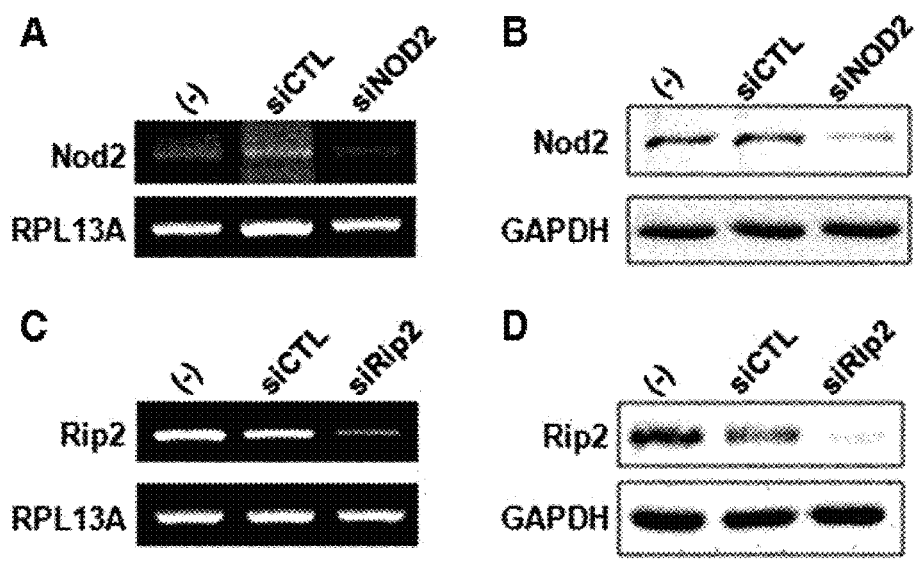
FIG. 8 demonstrates remarkable suppression of NOD2 and Rip2 genes and proteins expression in hUCB-MSG by respective siRNA.
Figure 9A:
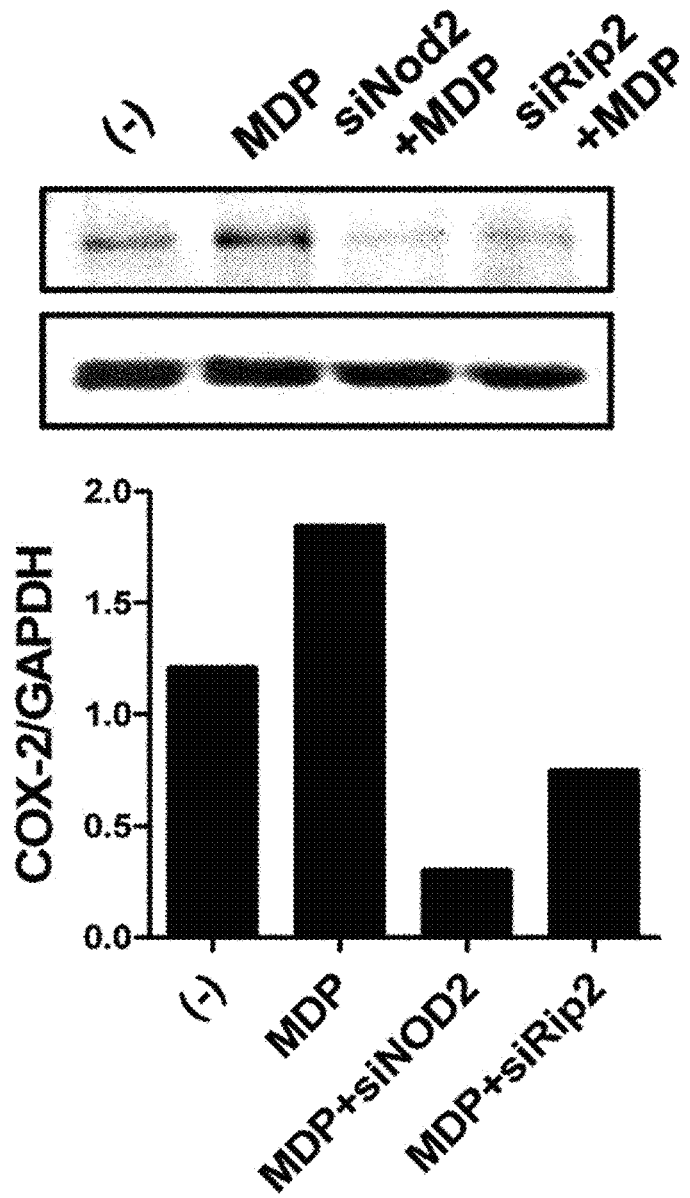
FIG. 9a shows COX-2 expression increased by treatment of siNOD2 and siRip2 with MDP.
Figure 9B:
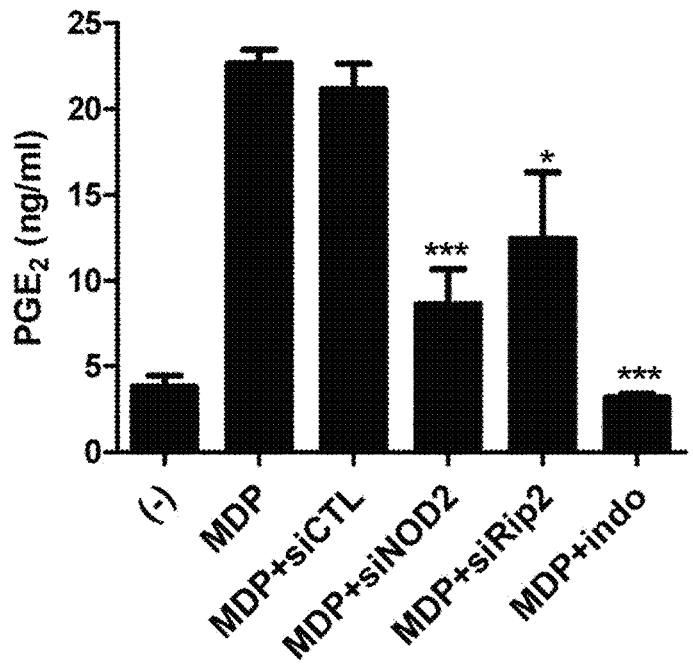
FIG. 9b shows PGE$_2$ secretion increased by treatment of siNOD2, siRip2 and indomethacin (indo) with MDP.
Figure 9C:
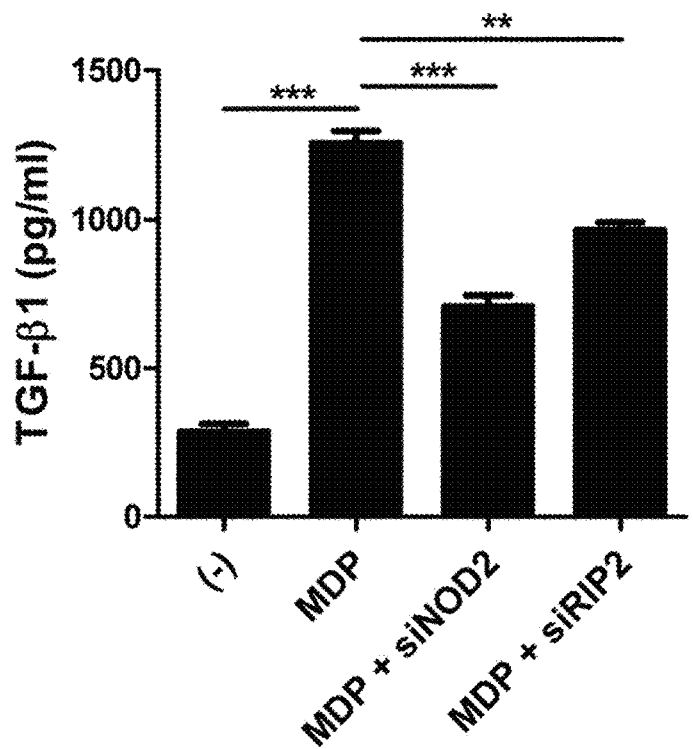
FIG. 9c shows TGF-β1 secretion increased by treatment of siNOD2 and siRip2 with MDP.
Figure 9D:
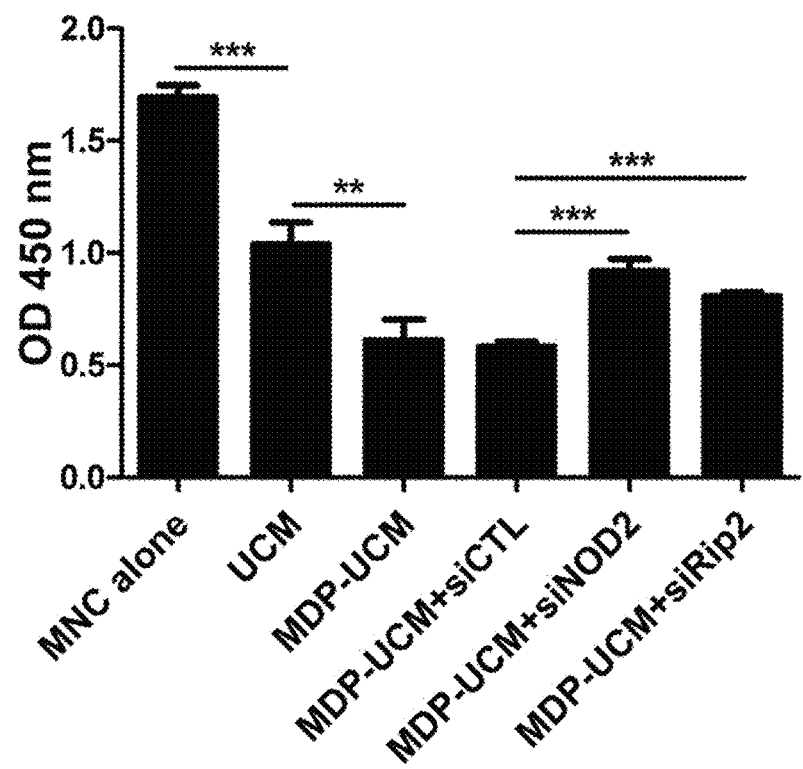
FIG. 9d is a graph showing the changes in inhibitory effect on MNC proliferation by treatment of siNOD2 and siRip2 with MDP.

The results demonstrated that the gene and protein expression of both NOD2 and Rip2 are remarkably suppressed by siRNAs in hUCB-MSCs (FIG. 8). Down-regulation of NOD2 and Rip2 by siRNA further suppressed MDP-induced COX-2 expression in hUCB-MSCs (FIG. 9a). The siRNA treatment of NOD2 and Rip2 reduced $PGE_2$ and TGF-β1 productions in MDP-UCM, as compared to the control siRNA (FIGS. 9b and 9c). Furthermore, MLR experiment showed that down-regulation of NOD2 and Rip2 restored the increased inhibitory effect of MDP-UCM against hMNC proliferation (FIG. 9d). These results suggest that MDP induces the increased production of $PGE_2$ and TGF-β1 in hUCB-MSCs via NOD2-Rip2 pathway, indicating enhancement of immunosuppressive ability of UCM-MSC.

Example 8

Analysis of the Effect of MDP-UCM on IL-10 Production and Regulatory T Cell Population in hMNCs 8-1: Investigation of the Effect of MDP-UCM on IL-10 Production in hMNCs $PGE_2$ produced in bone marrow stromal cells is known to take an important role in IL-10 production by host macrophages (Nemeth, K., A. et al., Bone marrow stromal cells attenuate sepsis via prostaglandin E(2)-dependent reprogramming of host macrophages to increase their interleukin-10 production. Nat Med 15:42-49, 2009). MDP induces $PGE_2$ production in hUCB-MSCs, and thus the present inventors examined whether IL-10 production in hMNCs is increased in the presence of MDP-UCM. The experiment was performed by the same method described in Example 5-6.

Figure 10A:
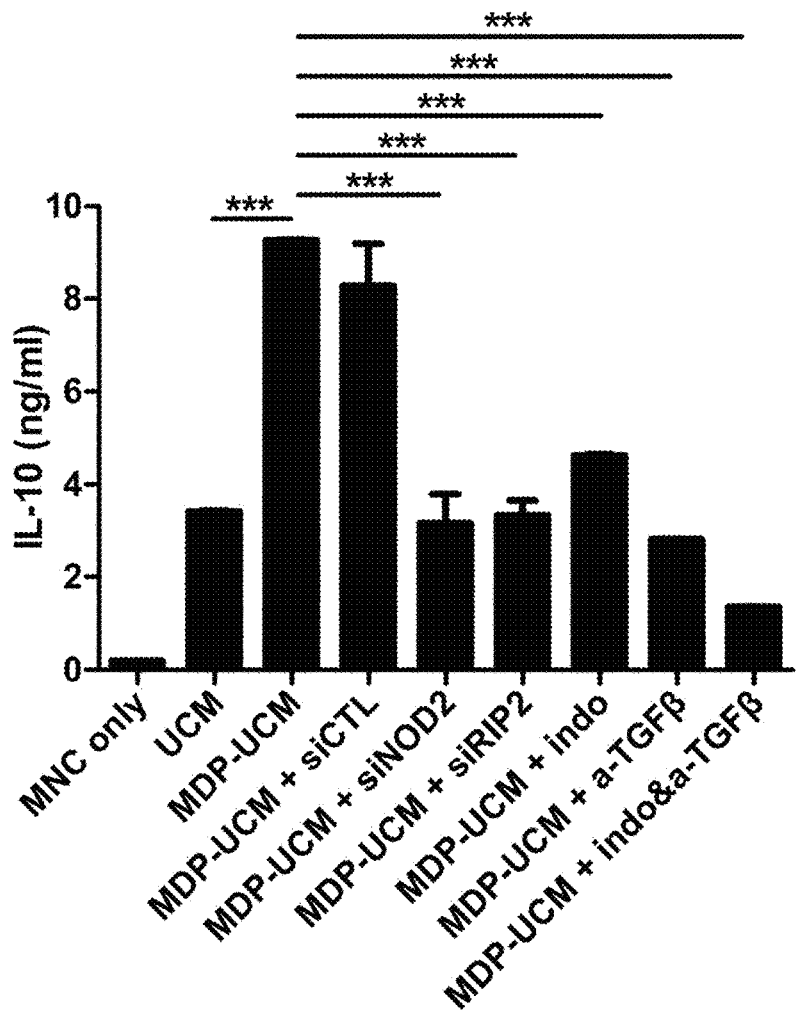
FIG. 10a shows IL-10 secretion enhanced by treatment of siNOD2, siRip2, indomethacin (indo) and TFG-β1 neutralizing antibody (a-TFG-β1) with MDP.

The results demonstrated that UCB-MSC alone did not produce IL-10, regardless of MDP stimulation (data not shown). Although hMNC alone did not produce IL-10, IL-10 production was up-regulated in the presence of UCM (FIG. 10a). Moreover, IL-10 production by hMNC was more increased in the presence of MDP-UCM than in the presence of the untreated UCM (FIG. 10a). However, the increased IL-10 production in hMNC by MDP-UCM was reversed by single treatment with indomethacin or TGF-β1 neutralizing antibody, and the above effect was accelerated by treating the cell with a combination of indomethacin and TGF-β1 neutralizing antibody (FIG. 10a). When NOD2 activity was suppressed by siRNA in hUCB-MSCs, IL-10 production in hMNC was not increased even in the presence of MDP-UCM, compared to non-treated UCM (FIG. 10a).

8-2: Investigation of the Effect of MDP-UCM on T Cell Population in hSNCs

Next, the present inventors investigated the effect of UCM on differentiation of hMNC into regulatory T cells (Treg). For this, hMNCs were cultured with UCM for 5 days, and co-expression of CD4, CD25, and Foxp3 in hMNCs was determined by Flow cytometry.

Figure 10B:
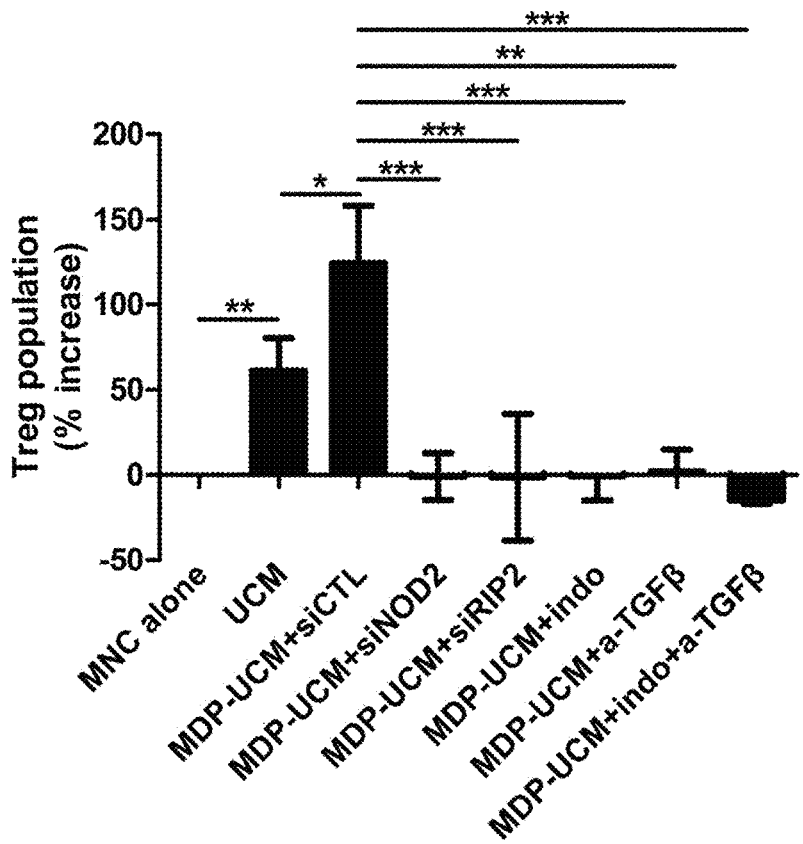
FIG. 10b shows the changes in Treg populations which are enhanced by treatment of siNOD2, siRip2, indomethacin (indo) and TFG-β1 neutralizing antibody (a-TFG-β1) with MDP.

The results demonstrated that Treg population in hMNCs was increased by 50 or more in the presence of UCM, and the increase in Treg population was higher in hMNCs cultured with MDP-UCM than in those cultured with untreated UCM (FIG. 10b). Similarly, the increase in Treg population by MDP-UCM was reversed by treatment with indomethacin and TGF-β1 neutralizing antibody or by NOD2 inhibition with siRNA (FIG. 10b). These results indicate that MDP-induced production of $PGE_2$ and TGF-β1 in UCM is important in IL-10 production by hMNC and differentiation of hMNC into Treg.

Example 9

Determination of NOD2 Expression in Other Types of Stem Cells

In order to determine whether immune and inflammatory responses can be regulated by the interaction between NOD2 receptor and agonist for other types of stem cells by addition of Nucleotide-binding Oligomerization Domain protein 2 (NOD2) agonist, NOD2 expressions in adipose tissue-derived stem cells (AD-MSC) and amniotic epithelial stem cells (AEC) were examined using a human monocytic leukemia cell line, i.e. THP-1 as a positive control group. RT-PCR was performed under the same condition described in Example 2. Human amniotic epithelial stem cells were obtained after delivery, with the written informed consent of the patient approved by the Guro Hospital (the Seoul National University IRB (IRB No. 0611/001-002), and amniotic epithelial stem cells were isolated from the obtained amnion tissue. The adipose tissue-derived stem cells were obtained, with the written informed consent of the patient approved by the Boramae Hospital (SNU IRB #0600/001-001), and the adipose tissue-derived stern cells were isolated and cultured.

Figure 11:
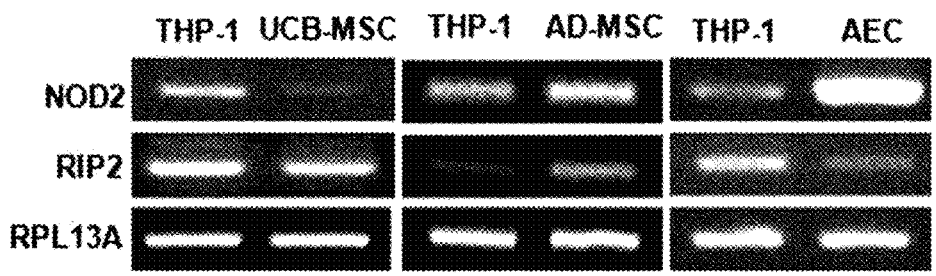
FIG. 11 shows mRNA RT-PCR result demonstrating NOD2, RIP2 and RPL13A expressions in umbilical cord blood-derived mesenchymal stem cells (UCB-MSC), adipose tissue-derived stem cells (AD-MSC) amniotic epithelial stem cells (AEC)

As shown in FIG. 11, NOD2 expression was higher in adipose tissue-derived stem cells and amniotic epithelial stem cells than in the positive control i.e., THP-1 cells. In other words, NOD2 receptor expression was observed in other types of stem cells as well as in mesenchymal stem cells, suggesting that other types of stem cells can be also used to regulate immune and inflammatory responses via NOD2 receptor-agonist interaction.

Example 10

Investigation of the Therapeutic Effects of NOD2-Expressing Stem Cells Using Colitis Animal Model 10-1: Investigation of the Therapeutic Effects of NOD2-Expressing Stem Cells Using Colitis Animal Model The present inventors examined whether hUCB-MSC treatment is effective for treatment of colitis mouse and whether MDP stimulation promotes protective effects of hUCB-MSC on DSS-induced colitis. For administration of hUCB-MSC, cells were cultured in the presence or absence of MDP for 24 hours, and then washed with PBS to remove MDP. To be specific, in order to investigate the therapeutic effects of MDP-treated stem cells in colitis animal models, colitis was induced in mice (Central Lab. Animal Inc., C57BL/6N) by treatment with 3% DSS (dextran sulfate sodium). After 2 days of treatment, MDP-treated hUCB-MSC, non-treated hUCB-MSC, and NOD2-suppressed hUCB-MSC by treatment with siRNA were intraperitonealy injected. At this time, 3% DSS was administered in drinking water for 7 days.

Figure 12A:
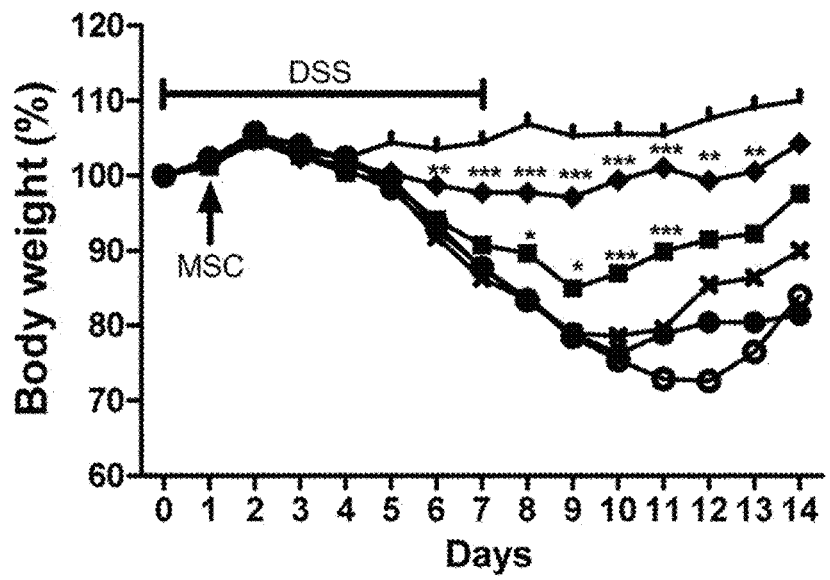
FIG. 12a is a graph showing body weight reduction in experimental groups and control groups of colitis model.
Figure 12B:
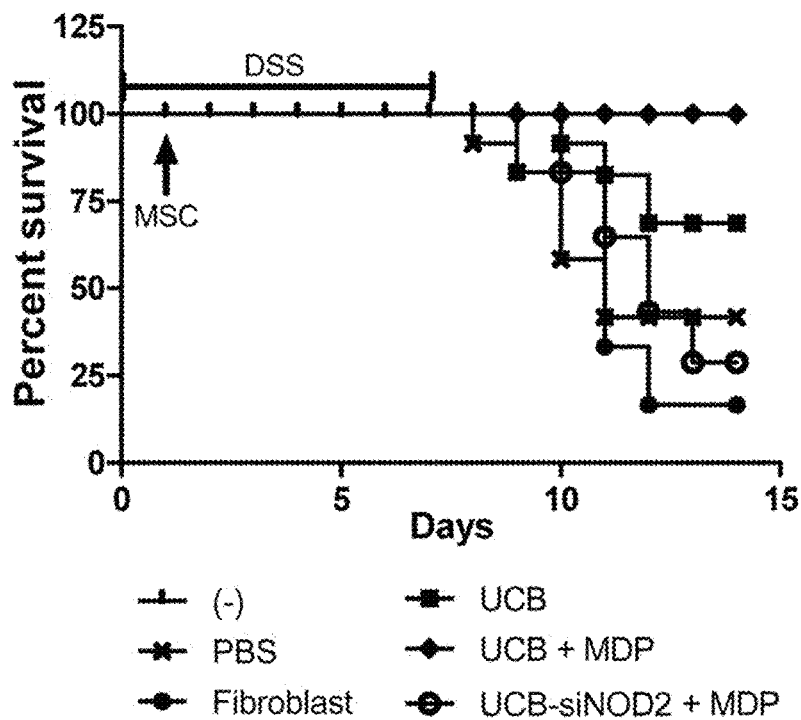
FIG. 12b is a graph showing survival rate.
Figure 12C:
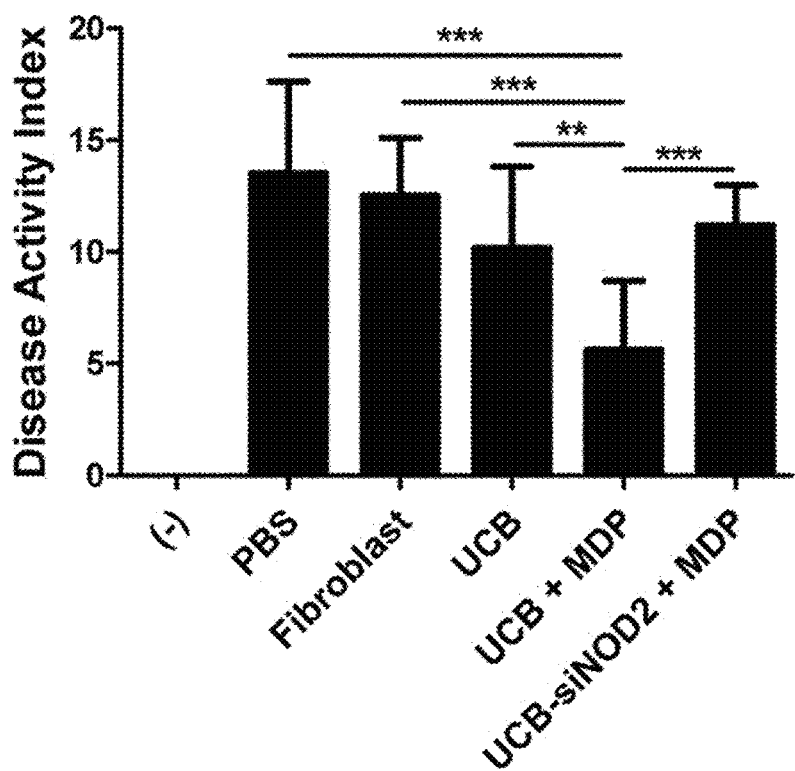
FIG. 12c is a graph showing the changes in disease activity index.

The results demonstrated that intraperitoneal injection of non-treated hUCB-MSC alleviated the body weight reduction and also improved survival rate of DSS-induced colitis mouse, as compared to PBS- or fibroblast-treated mouse (FIGS. 12a and 12b). Moreover, injection of MDP-stimulated hUCB-MSC (MDP-MSC) led to recovery of the body weight to 90% of the control group which was free of colitis, and none of the mice died from colitis (FIGS. 12a and 12b). Disease activity index was slightly reduced by injection of hUCB-MSC, but it was significantly different from that of PBS- or fibroblast-treated group. On the other hand, injection of MDP-MSC significantly reduced disease activity index (FIG. 12c). When NOD2 was down-regulated by siRNA, MDP-MSC did not alleviate body weight reduction, or increase survival rate and disease activity index.

Figure 12D:
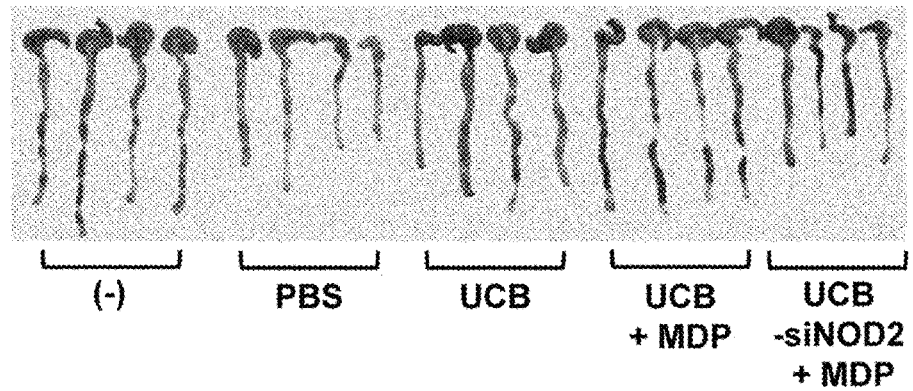
FIG. 12d shows the image, of colon length.
Figure 12E:
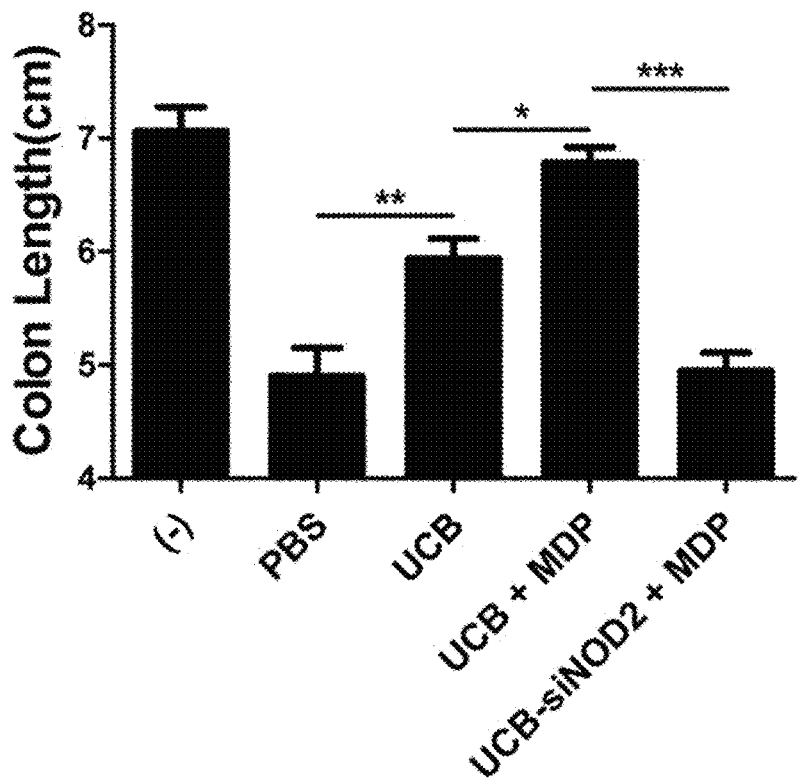
FIG. 12e is a graph showing the colon length.
Figure 12F:
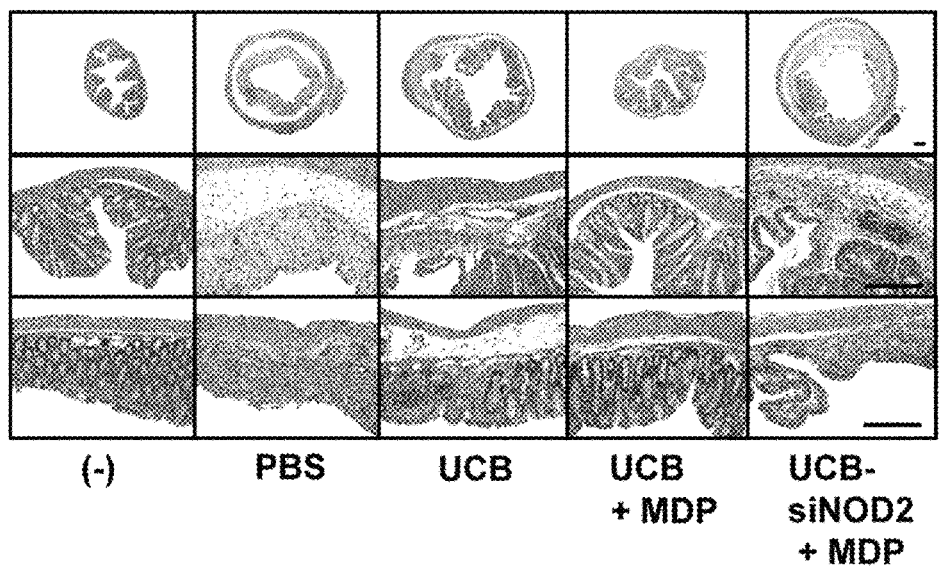
FIG. 12f is a histopathological image, showing inflammation, edema, and infiltration of inflammatory cells.
Figure 12G:
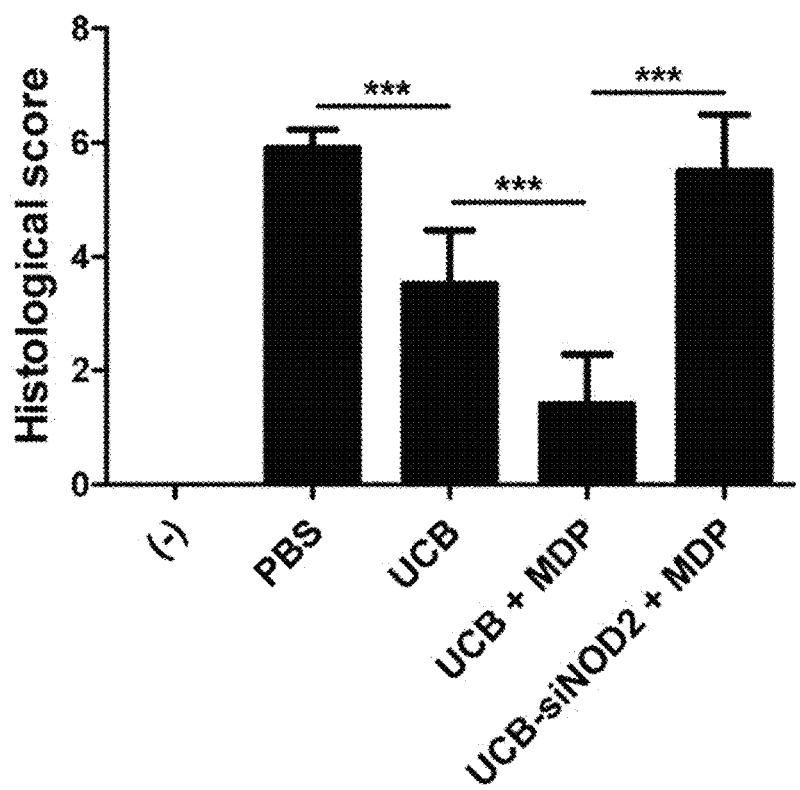
FIG. 12g is a graph showing pathological scores.

Mice were sacrificed on the 14$^{th}$ day to measure their colon length, and histopathological analysis was performed. The results of gross examination showed that the reduced colon length by inflammation was slightly alleviated by treatment with hUCB-MSC, which was enhanced by addition of MDP (FIGS. 12d and 12e). The results of histopathological study showed that colonic mucosal erosions, severe edema lesions, and inflammatory cell infiltration of the lamina propria and submucosal layer were observed in DSS-treated mice (FIG. 12f). The mucosal erosions of the submucosal layer and edema confined to a part of the colon were observed in hUCB-MSC-treated mice (FIG. 12f). However, the pathologic damages in the colons were completely treated and pathological scores were remarkably reduced by treatment with MDP-MSC (FIGS. 12f and 12g). As expected, injection of siNOD2-treated hUCB-MSC neither relieved pathological severity nor reduced pathological scores in DSS-induced colitis (FIGS. 12f and 12g). These results suggest that MDP enhances the protective effect of hUCB-MSC on colitis, indicating a critical role of NOD2.

10-2: Investigation of the Effect of MDP on Inflammatory Cytokine Production and T Cell Populations in Colitis Animal Model Furthermore, the present inventors investigated the effect of MDP on the regulation of hUCB-MSC-induced inflammatory cytokine production in colitis mouse.

Figure 13A:
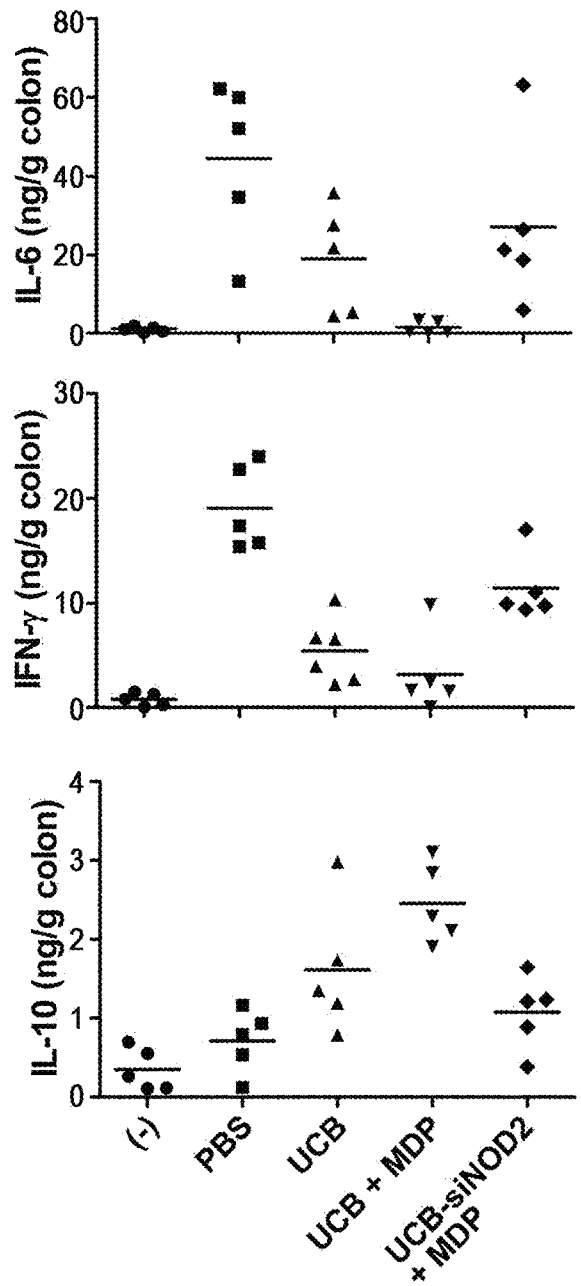
FIG. 13a is a graph showing changes in IL-6, IFN-γ and IL-10 secretion by MDP in the colon of DSS-induced colitis mouse model.

The results showed that hUCB-MSCs reduced IL-6 and IFN-γ productions and increased IL-10 production in DSS-treated mouse colons (FIG. 13a). Moreover, MDP-MSC blocked IL-6 and IFN-γ productions almost completely and promoted IL-10 production in DSS-treated mouse colons, but this effect was counteracted by NOD2 down-regulation (FIG. 13a).

In order to determine whether hUCB-MSCs have an effect on Treg populations in the mouse colon, Foxp3+ cell infiltration into colon was monitored under a fluorescence microscope.

Figure 13B:
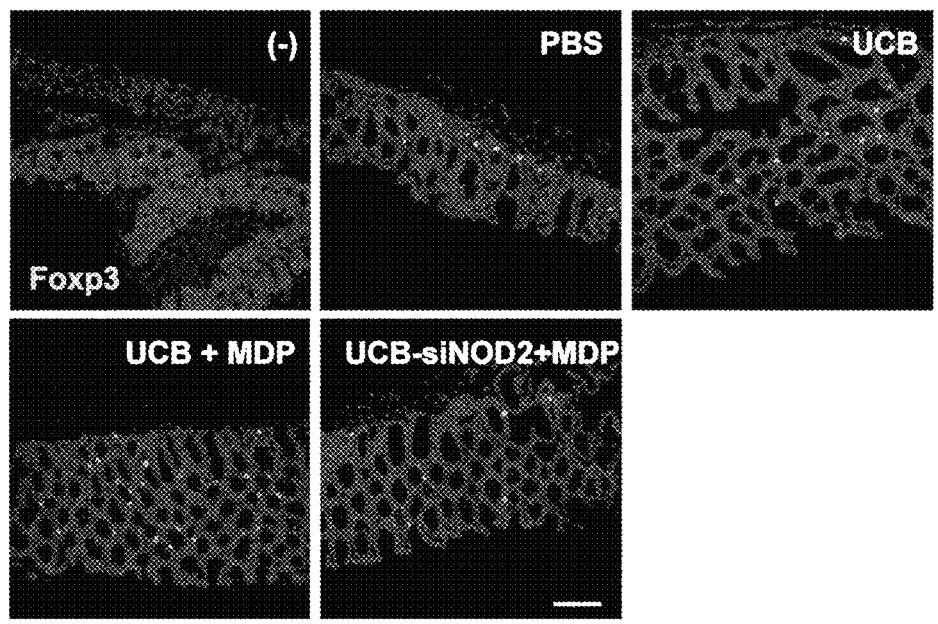
FIG. 13b is a fluorescence microscopic image showing. Fox3p+ localization in the colons of control groups and experimental groups of colitis mouse model after MDP and siNOD2 treatment.
Figure 13C:
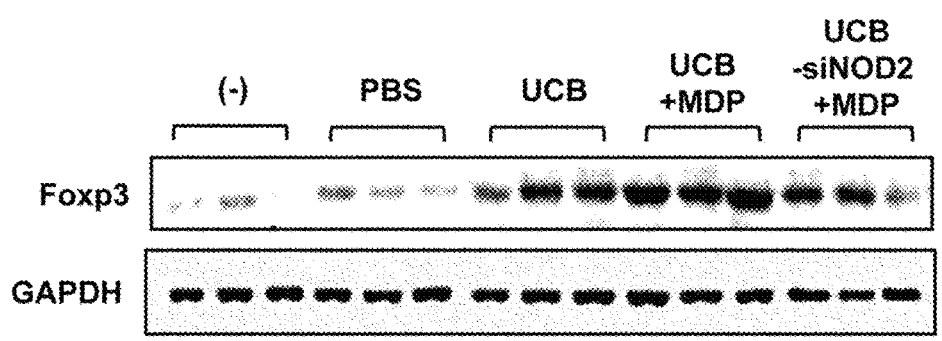
FIG. 13c is the result of Western blotting showing Fox3p protein expression level in control groups and experimental groups after MDP and siNOD2 treatment.
Figure 13D:
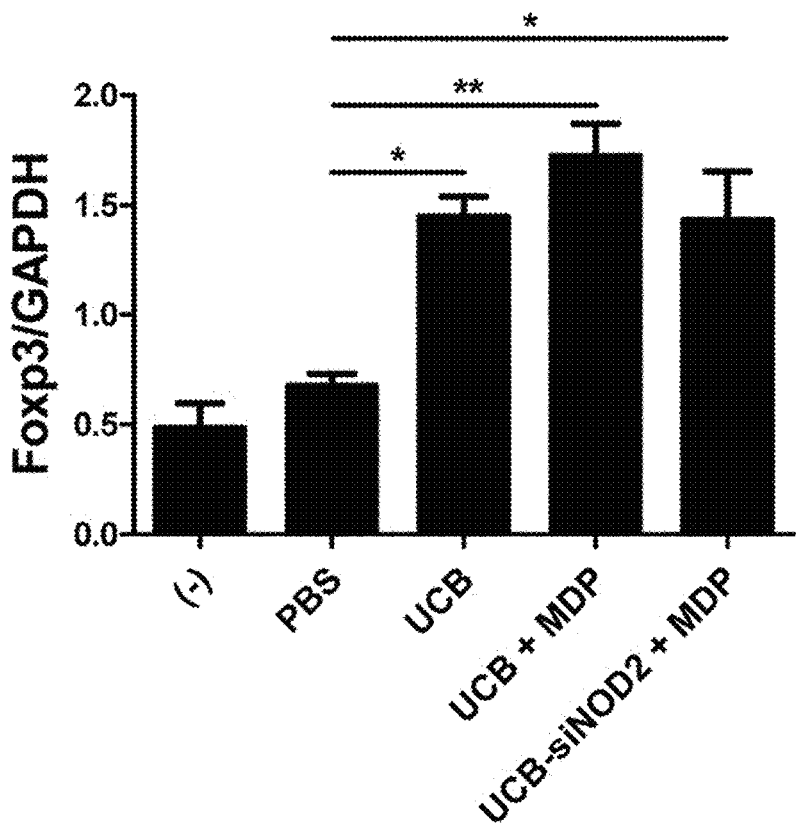
FIG. 13d shows the quantification of the Western blot analysis.

The results demonstrated that localization of Fox3p+ cells in the colon was higher in hUCB-MSC-treated colitis mice than in PBS-treated colitis mice (FIG. 13b). In addition, localization of Fox3p+ cells in the colon was increased further by treatment with MDP-MSC, which was counteracted by NOD2 inhibition in hUCB-MSC (FIG. 13b). The Foxp3 expression in the colon was quantified by Western blotting. Foxp3 protein expression was higher in hUCB-MSC-treated mice than in PBS-treated colitis mice (FIGS. 13c and 13d). Similarly, Foxp3 level in the colon was increased further by treatment with MDP-MSC, which was also counteracted by NOD2 down-regulation (FIGS. 13c and 13d).

10-3: Analysis of Inflammatory Cell Infiltration in Colitis Animal Model

Lastly, the present inventors examined inflammatory cell infiltration into mouse colon. The activity of myeloperoxidase (MPO) was monitored to determine neutrophilic infiltration.

Figure 13E:
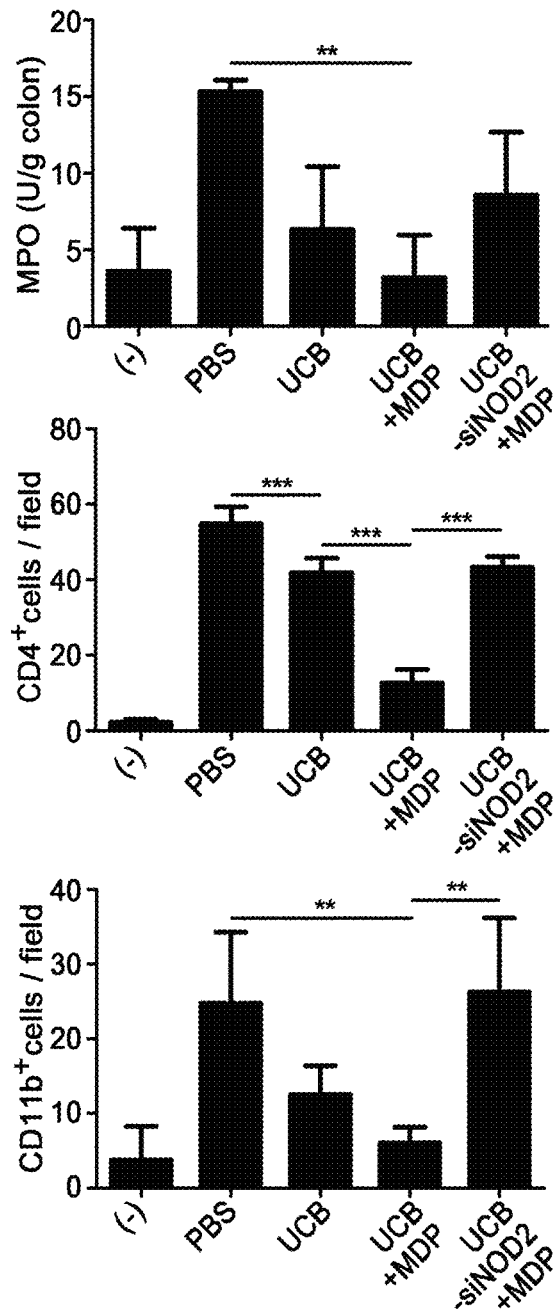
FIG. 13e is a graph demonstrating MPO activity and CD4+, CD11b+ cell infiltration for analyzing infiltration of inflammatory cells in mouse colon.

The results demonstrated that hUCB-MSC suppressed MPO activity and CD4+ and CD11b+ cell infiltration into the DSS-treated mouse colon (FIG. 13e). Likewise, MDP-MSC suppressed MPO activity and CD4+ and CD11b+ cell infiltration to a greater extent, which was counteracted by NOD2 inhibition by siRNA (FIG. 13e).

These results support that hUCB-MSC induces anti-inflammation while suppressing pro-inflammatory response, which can be enhanced by MDP treatment in a NOD2-dependent manner.

Furthermore, these results suggest that the MDP-treated stem cells of the present invention or the culture thereof can be practically used for the treatment of inflammation in animal models having colitis.

Example 11

Investigation of the Therapeutic Effect of MDP-Treated hUCB-MSC on Atopic Dermatitis-Induced Animal Model 11-1: Induction of Atopic Dermatitis and Treatment with hUCB-MSC Injection One day before conducting the present experiment, the hair on the back of 8-week-old female NC/Nga mouse was shaved, and the remaining hair on the back skin was completely removed by applying a hair removal cream. Then the next day, 150 μl of 4% sodium dodecyl sulfate (SDS) aqueous solution was applied to the shaved back skin to remove fat from the skin. The skin was completely dried for approximately 3 to 4 hours, and then 100 mg of *Dermatophagoides farina* (Df) extract was applied evenly to the back and ears. Application of Df extract was performed twice a week for 3 weeks for a total of 6 times (application of SDS aqueous solution is essential for every application of Df extract) to induce atopic dermatitis. Then, 2×10$^6$ hUCB-MSCs prepared in Example 1 was suspended in 200 μl of phosphate buffered saline (PBS), and intravenously or subcutaneously injected to NC/Nga mouse once a week for 3 weeks during Df application and 1 week after induction of atopic dermatitis, i.e. a total of 4 times for 4 weeks. MDP-treated hUCB-MSCs were prepared by culturing hUCB-MSCs in a medium supplemented with 10 μl/mL of MDP for 24 hours, and then by washing the cells with PBS 5 times prior to injection.

11-2: Investigation of the Therapeutic Effect of MDP-Treated hUCB-MSC by Gross Examination of the Lesion In order to investigate the therapeutic effect of the MDP-treated hUCB-MSCs on atopic dermatitis, an autopsy was conducted after 24 hours of the 4$^{th}$ injection of hUCB-MSCs, and severity of the lesion was evaluated by gross examination. The gross examination was conducted in accordance with dryness, excoriation, erythema, and edema giving a score of 0 to 3, and the total score was used for evaluation.

Figure 14:
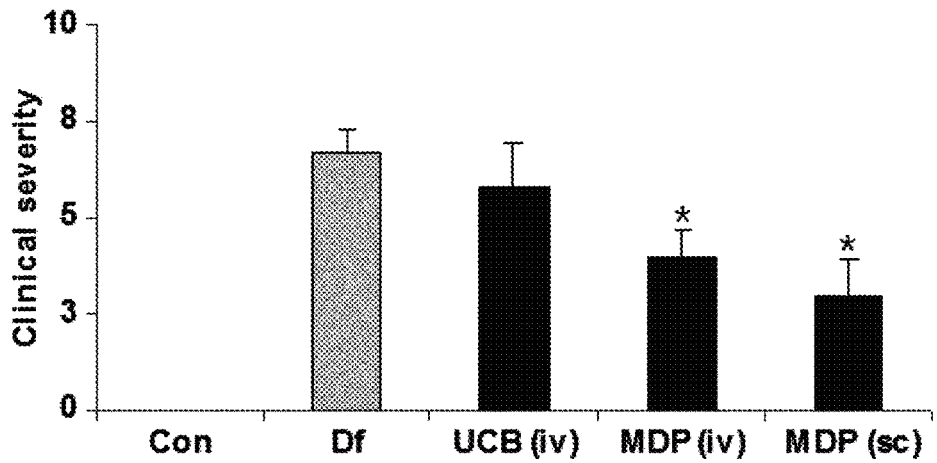
FIG. 14 is a graph showing the result of gross examination after intravenous or subcutaneous injections of MDP-treated hUCB-MSC into atopic dermatitis-induced mouse.

As shown in FIG. 14, intravenous injection of hUCB-MSC into atopic dermatitis-induced group induced a slight alleviation of lesions, not having a great difference from non-treated atopic dermatitis-induced group. In contrast, significant alleviation of lesions was observed in the groups that had intravenous or subcutaneous injection of MDP-treated hUCB-MSC.

These results suggest that the MDP-treated stem cells of the present invention or the culture thereof can be used for the treatment of autoimmune diseases such as atopic dermatitis.

11-3: Investigation of the Therapeutic Effect of MDP-Treated hUCB-MSC by Analysis of Serum IgE In order to investigate the therapeutic effect of MDP-treated hUCB-MSCs on atopic dermatitis, an autopsy was conducted after 24 hours of the 4$^{th}$ injection of hUCB-MSCs, and IgE level in the serum collected from autopsy was measured using a commercial Opt EIA mouse set (BD Bioscience, Mississauga, Canada).

Figure 15:
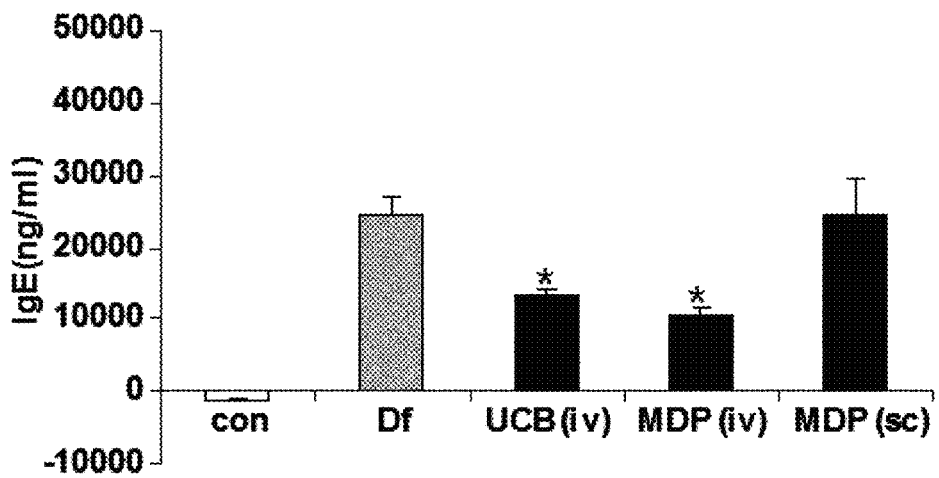
FIG. 15 is a graph showing a serum immunoglobulin E level, which is an index of atopic dermatitis.

As shown in FIG. 15, a significant inhibition of IgE was observed in the groups that had intravenous injections of hUCB-MSC or MDP-treated hUCB-MSC, while a higher inhibition rate was observed in the group that had intravenous injection of MDP-treated hUCB-MSC. However, subcutaneous injection of MDP-treated hUCB-MSC did not induce a great difference from the atopic dermatitis-induced group.

11-4: Investigation of the Therapeutic Effect of MDP-Treated hUCB-MSC by Analysis of Serum IgG1

In order to investigate the therapeutic effect of MDP-treated hUCB-MSCs on atopic dermatitis, an autopsy was conducted after 24 hours of the 4$^{th}$ injection of hUCB-MSCs, and IgG1 level which is a representative index for a Th2 immune response of atopic dermatitis was measured in the serum collected from autopsy using an ELISA kit (Bethyl Laboratories Inc., Montgomery, Tex., USA).

Figure 16:
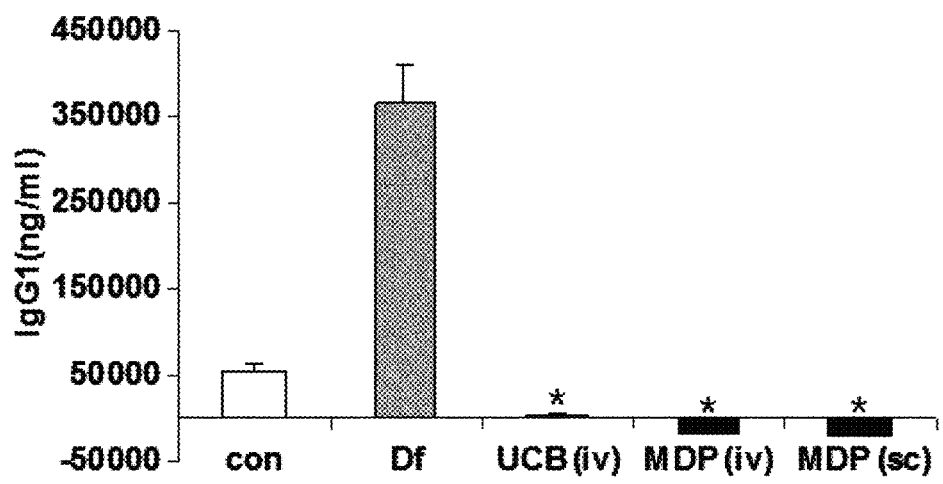
FIG. 16 is a graph showing a serum immunoglobulin G1 level, which is an index of atopic dermatitis.

As shown in FIG. 16, a significant inhibition of IgG1 was observed in all of the hUCB-MSC-treated groups.

11-5: Investigation of the Therapeutic Effect of MDP-Treated hUCB-MSC by Histopathological Examination of Skin Tissue In order to investigate the therapeutic effect of MDP-treated hUCB-MSCs on atopic dermatitis, an autopsy was conducted after 24 hours of the 4$^{th}$ injection of hUCB-MSCs, and the skin tissues were collected and fixed with a 1.0% neutral formalin solution. Then, the tissue slices were processed, paraffin-embedded, and cut into 3 to 4 μm sections. Then, hematoxylin-eosin (H&E) staining was performed for pathological study.

Figure 17:
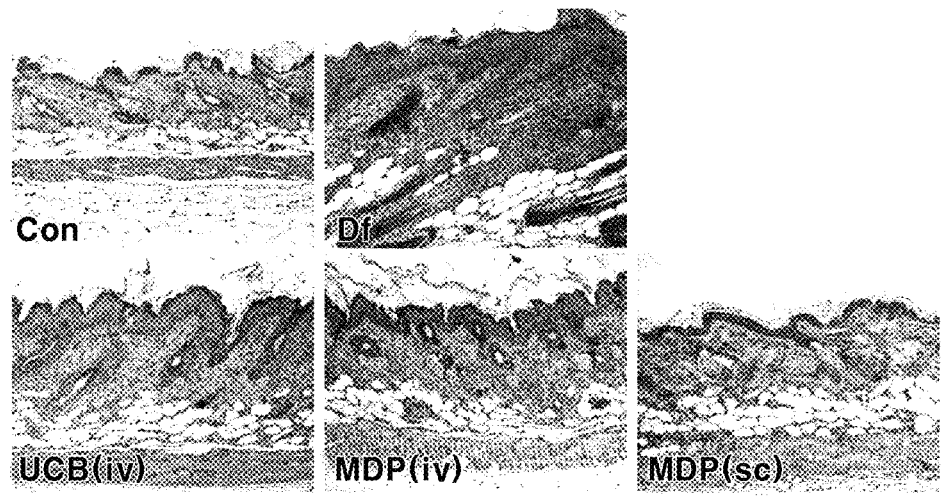
FIG. 17 is an image of H&E, staining after tissue processing of the mouse skin tissue.

As shown in FIG. 17, epidermal hyperplasia and excessive infiltration of inflammatory cells were observed in the atopic dermatitis-induced group. Reductions in epidermal thickness and infiltration of inflammatory cells were observed in intravenous injection of hUCB-MSC, and intravenous or subcutaneous injection of MDP-treated hUCB-MSC. The greatest rate of alleviation of lesions was observed in subcutaneous injection of MDP-treated hUCB-MSC, intravenous injection of MDP-treated hUCB-MSC, and intravenous injection of hUCB-MSC in that order.

11-6: Investigation of the Therapeutic Effect of MDP-Treated hUCB-MSC by Histopathological Examination of Skin Tissue In order to investigate the therapeutic effect of MDP-treated hUCB-MSCs on atopic dermatitis, an autopsy was conducted after 24 hours of the 4$^{th}$ injection of hUCB-MSCs, and the skin tissues were collected and fixed with a 10% neutral formalin solution. Then, the tissue slices were processed, paraffin-embedded, and cut into 3-4 μm sections. Then, Toluidine blue staining was performed to examine mast cell degranulation, which is one of the major symptoms of atopic dermatitis.

Figure 18:
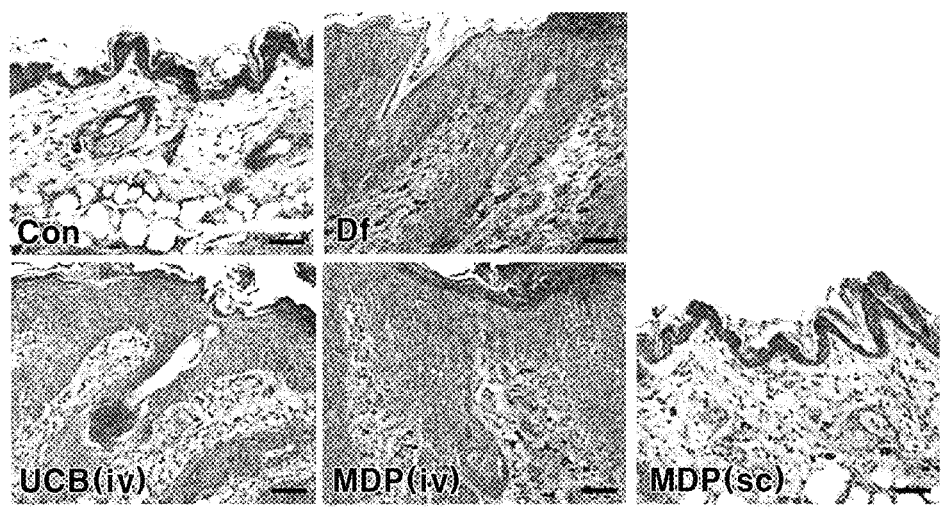
FIG. 18 is an image showing mast cell degranulation, which is one of the major symptoms of atopic dermatitis, after tissue processing and Toluidine blue staining of the mouse skin tissue.

As shown in FIG. 18, a large number of degranulated mast cells were observed in the atopic dermatitis-induced group, and reduction in mast cell degranulation was observed in all of the other groups.

These results suggest that the MDP-treated stem cells of the present invention or the culture thereof can be practically used for the treatment of immune disorders in animal models such as atopic dermatitis.

Unless otherwise specified, all technical and scientific terms used herein have the same meaning as commonly understood by those of ordinary skill in the art, to which this invention belongs. The nomenclature used herein are also well known and commonly used in the art.

EFFECT OF THE INVENTION

The present invention provides a pharmaceutical composition that can be used for the prevention or treatment of immune disorders and inflammatory diseases. Furthermore, the present invention provides a method for preparing PGE$_2$ and TGF-β1, which is able to produce PGE$_2$ and TGF-β1 at high yield in a cost-effect way without performing chemical processing.

The pharmaceutical composition of the present invention is an inexpensive cellular therapeutic agent having no side-effects, which can be used as an alternative to the previously known immunosuppressive drugs and anti-inflammatory drugs having side-effects. Therefore, it can be used for the prevention or treatment of immune disorders such as autoimmune diseases including Crohn's disease, rheumatoid arthritis, and atopic dermatitis, and inflammatory diseases.

What is claimed is:

1. A method for suppressing immune responses or inflammatory responses of a subject comprising the steps of
   (a) determining expression of Nucleotide-binding Oligomerization Domain protein 2 (NOD2) in isolated mesenchymal stem cells;
   (b) treating the cells expressing NOD2 with a NOD2 agonist to increase the production of prostaglandin E2 (PGE2) or transforming growth factor beta 1 (TGF-β1) and culturing them; and
   (c) providing the cells producing PGE2 or TGF-β1 of step (b) or a culture thereof to the subject.

2. The method according to claim 1, wherein the method suppresses inflammatory responses of a subject.

3. The method according to claim 1, wherein the suppression of immune responses inflammatory responses is accomplished by activation NOD2-Rip2 pathway.

4. The method according to claim 1, wherein the NOD2 agonist is muramyl dipeptide (MDP).

5. The method according to claim 1, wherein the mesenchymal stem cells or a culture thereof perform as an immunosuppressive drug or an anti-inflammatory drug.

6. The method according to claim 1, wherein the concentration of the NOD2 agonist in a culture medium is 1 to 100 μg/ml, and incubation time after addition of the NOD2 agonist is 0.1 to 200 hours.

7. The method according to claim 1, wherein the mesenchymal stem cells secrete prostaglandin $E_2$ ($PGE_2$) or transforming growth factor beta 1 (TGF-β1) during the culturing, and wherein the culture thereof comprises $PGE_2$ or TGF-β1.

* * * * *